(12) United States Patent
Mohapatra et al.

(10) Patent No.: US 8,349,604 B2
(45) Date of Patent: Jan. 8, 2013

(54) NANO-BASED DEVICE FOR DETECTION OF DISEASE BIOMARKERS AND OTHER TARGET MOLECULES

(75) Inventors: Shyam S. Mohapatra, Lutz, FL (US); Arun Kumar, Tampa, FL (US)

(73) Assignee: University of South Florida, Tampa, FL (US)

( * ) Notice: Subject to any disclaimer, the term of this patent is extended or adjusted under 35 U.S.C. 154(b) by 699 days.

(21) Appl. No.: 11/747,713

(22) Filed: May 11, 2007

(65) Prior Publication Data
US 2008/0023325 A1    Jan. 31, 2008

Related U.S. Application Data

(63) Continuation-in-part of application No. 11/747,125, filed on May 10, 2007.

(60) Provisional application No. 60/814,679, filed on Jun. 15, 2006.

(51) Int. Cl.
*C12M 1/34* (2006.01)

(52) U.S. Cl. ............. 435/287.2; 422/82.01; 204/403.01; 204/280; 977/762; 977/810; 436/150

(58) Field of Classification Search ............. 204/403.01, 204/403.14, 280; 977/762, 810; 422/68.1, 422/82.01; 435/7.1, 287.1, 287.2; 436/512, 436/149–151
See application file for complete search history.

(56) References Cited

U.S. PATENT DOCUMENTS

| 4,128,629 | A |   | 12/1978 | Eldred et al. |
|---|---|---|---|---|
| 4,791,057 | A | * | 12/1988 | Misaki et al. .................... 435/26 |
| 5,478,755 | A |   | 12/1995 | Attridge et al. |
| 5,672,480 | A | * | 9/1997 | Dowell et al. .................. 435/7.4 |
| 6,239,255 | B1 |  | 5/2001 | Furlong et al. |
| 6,325,904 | B1 |  | 12/2001 | Peeters |
| 6,833,274 | B2 |  | 12/2004 | Lawrence et al. |
| 6,942,771 | B1 |  | 9/2005 | Kayyem |
| 7,135,295 | B1 |  | 11/2006 | Willner et al. |
| 2003/0077642 | A1 | * | 4/2003 | Fritsch et al. ..................... 435/6 |
| 2003/0118453 | A1 | * | 6/2003 | Fritsch et al. ................... 417/48 |
| 2003/0134332 | A1 | * | 7/2003 | Boykin, Jr. ..................... 435/7.1 |

FOREIGN PATENT DOCUMENTS

| WO | WO 02/054052 | 7/2002 |
|---|---|---|
| WO | WO 2005/024382 | 3/2005 |

OTHER PUBLICATIONS

Cook, C. J., "Real-time measurements of corticosteroids in conscious animals using an antibody-based electrode", Nature Biotechnology, vol. 15, May 1997, p. 467-471.*

Ji, C., and P. C. Searson, "Fabrication of nanoporous gold nanowires", Applied Physics Letters, vol. 81, No. 23, Dec. 2002, p. 4437-4439.*

(Continued)

*Primary Examiner* — J. Christopher Ball
(74) *Attorney, Agent, or Firm* — Saliwanchik, Lloyd & Eisenschenk

(57) ABSTRACT

The present invention pertains to a nano-based sensing device (a sensor) comprising a nano-scale working electrode that can be used for the ultra-sensitive detection of blood analytes, disease biomarkers, and other target molecules. The present invention also pertains to a method for detecting target molecules using the sensor as the sensor element of a microfluidic device.

32 Claims, 16 Drawing Sheets

(D) CROSS-SECTION SCHEMATIC OF THE TEST CELL

OTHER PUBLICATIONS

Electrochemistry Group Hydrodynamic Device Webpage; http://www.cheng.cam.ac.uk/research/groups/electrochem/Java/electrochemistry/ELED/17html/hydro.html; published Mar. 5, 2004.*

Amendola, L. et al. "Determination of Endogenous and Synthetic Glucocorticoids in Human Urine by Gas Chromatography-Mass Spectrometry Following Microwave-Assisted Derivatization" *Analytica Chimica Acta*, 2003, pp. 233-243, vol. 489.

Appel, D. et al. "A Fluorimetric Assay for Cortisol" *Anal Bioanal Chem*, 2005, pp. 182-186, vol. 383.

Attili, B.S. et al. "A Piezoelectric Immunosensor for the Detection of Cortisol" *Analytical Letters*, 1995, pp. 2149-2159, vol. 28, No. 12.

Diaz-González, M. et al. "Recent Advances in Electrochemical Enzyme Immunoassays" *Electroanalysis*, 2005, pp. 1901-1918, vol. 17, No. 21.

Kandimalla, V.B. et al. "Immobilization of Biomolecules in Sol-Gels: Biological and Analytical Applications" *Critical Reviews in Analytical Chemistry*, 2006, pp. 73-106, vol. 36.

Kartsova, L.A. et al. "Determination of Steroids in Biological Samples by Micellar Electrokinetic Chromatography" *Journal of Analytical Chemistry*, 2007, pp. 76-84, vol. 62, No. 1.

Kushnir, M.M. et al. "Cortisol and Cortisone Analysis in Serum and Plasma by Atmospheric Pressure Photoionization Tandem Mass Spectrometry" *Clinical Biochemistry*, 2004, pp. 357-362, vol. 37.

Kumar, A. et al. "Ultrasensitive Detection of Cortisol with Enzyme Fragment Complementation Technology Using Functionalized Nanowire" *Biosensors and Bioelectronics*, 2007, pp. 2138-2144, vol. 22.

Lentjes, E.G.W.M. et al. "Free Cortisol in Serum Assayed by Temperature-Controlled Ultrafiltration Before Fluorescence Polarization Immunoassay" *Clinical Chemistry*, 1993, pp. 2518-2521, vol. 39, No. 12.

Leung, W. et al. "One-step Quantitative Cortisol Dipstick with Proportional Reading" *Journal of Immunological Methods*, 2003, pp. 109-118, vol. 281.

Pei, R. et al. "A piezoelectric Immunosensor for Complement C4 Using Protein A Oriented Immobilization of Antibody" *J. Chem. Technol. Biotechnol*, 1998, pp. 59-63, vol. 73.

Raul, J. et al. "Detection of Physiological Concentrations of Cortisol and Cortisone in Human Hair" *Clinical Biochemistry*, 2004, pp. 1105-1111, vol. 37.

Rönquist-Nii, Y. et al "Determination of Corticosteroids in Tissue Samples by Liquid Chromatography-Tandem Mass Spectrometry" *Journal of Pharmaceutical and Biomedical Analysis*, 2005, pp. 341-360, vol. 37.

Skladal, P. "Piezoelectric Quartz Crystal Sensors Applied for Bioanalytical Assays and Characterization of Affinity Interactions" *J. Braz. Chem. Soc.*, 2003, pp. 491-502, vol. 14, No. 4.

Tang, D. et al. "Construction of a Novel Immunoassay for the Relationship Between Anxiety and the Development of a Primary Immune Response to Adrenal Corticol Hormone" *Bioprocess Biosyst Eng*, 2005, pp. 135-141, vol. 27.

Taylor, R.L. et al. "Quantitative, Highly Sensitive Liquid Chromatography-Tandem Mass Spectrometry Method for Detection of Synthetic Corticosteroids" *Clinical Chemistry*, 2004, pp. 2345-2352, vol. 50, No. 12.

Zhang, Y. et al. "Simultaneous Determination of Cortisol and Prednisolone in Body Fluids by Using HPLC-DAD Coupled with Second-Order Calibration Based on Alternating Trilinear Decomposition" *Journal of Chromatography B*, 2006, pp. 116-123, vol. 840.

Zhou, J.C. et al. "Immunoassays for Cortisol Using Antibody-Doped Sol-Gel Silica" *J. Mater. Chem.*, 2004, pp. 2311-2316. vol. 14.

Aravamudhan, S. et al. "Sensitive estimate of total cholesterol in blood using Au nanowires based micro-fluidic platform" *Biosensors and Bioelectronics*, 2007, Epub date Jan. 9, 2007, pp. 2289-2294, vol. 22, No. 9-10.

Kumar, A. et al. "Ultrasensitive Detection of Cortisol with Enzyme Fragment Complementation Technology Using Functionalized Nanowire" *Biosensors and Bioelectronics*, 2007, Epub date Nov. 9, 2006, pp. 2138-2144, vol. 22.

Boote, J.J. et al. "Dielectrophoretic manipulation and electrical characterization of gold nanowires", *Nanotechnology*, 2005, 16:1500-1505.

Papadakis, S.J. et al. "Dielectrophoretic assembly of reversible and irreversible metal nanowire networks and vertically aligned arrays", *Appl. Phys. Lett.*, 2006, 88:233118-1 to 233118-3.

* cited by examiner

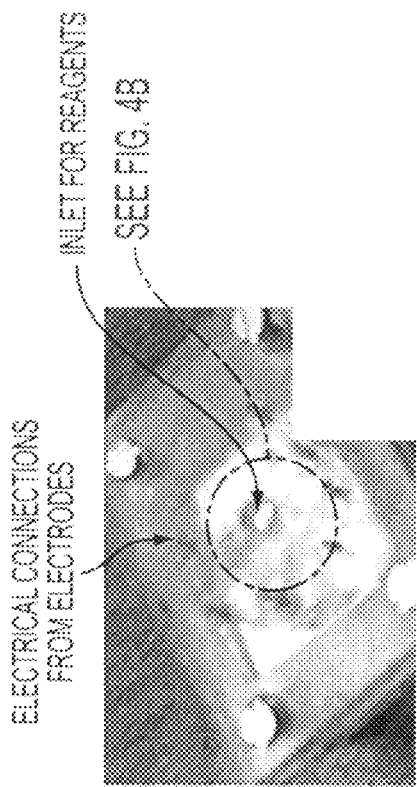
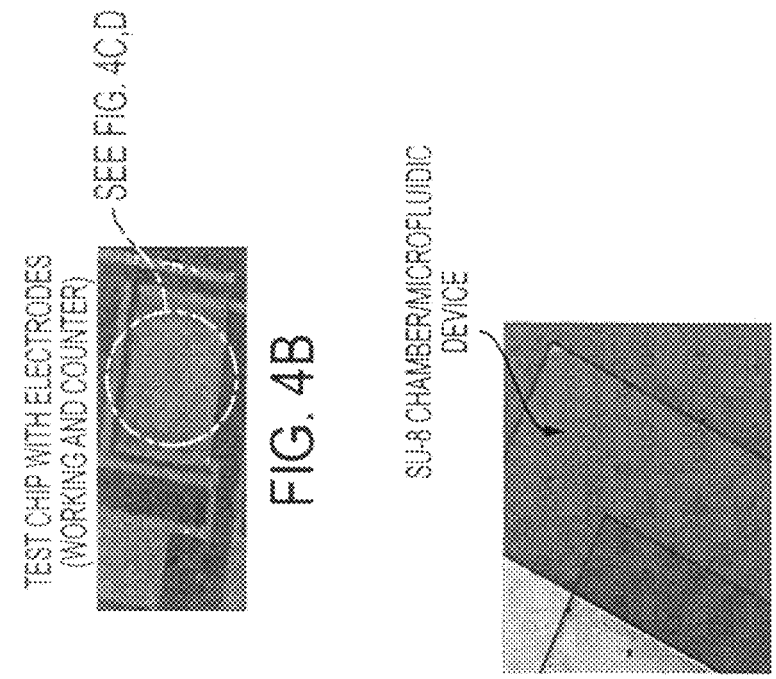
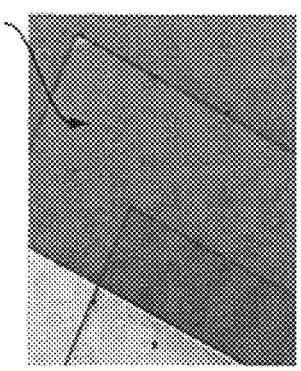
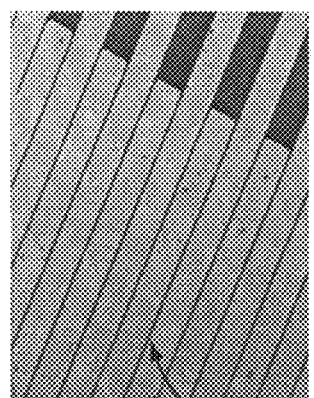
FIG. 4A — ELECTRICAL CONNECTIONS FROM ELECTRODES; INLET FOR REAGENTS; SEE FIG. 4B
FIG. 4B — TEST CHIP WITH ELECTRODES (WORKING AND COUNTER); SEE FIG. 4C,D
FIG. 4C — "ASSEMBLY LINES" FOR PLACEMENT OF Au NANOWIRES
FIG. 4D — SU-8 CHAMBER/MICROFLUIDIC DEVICE

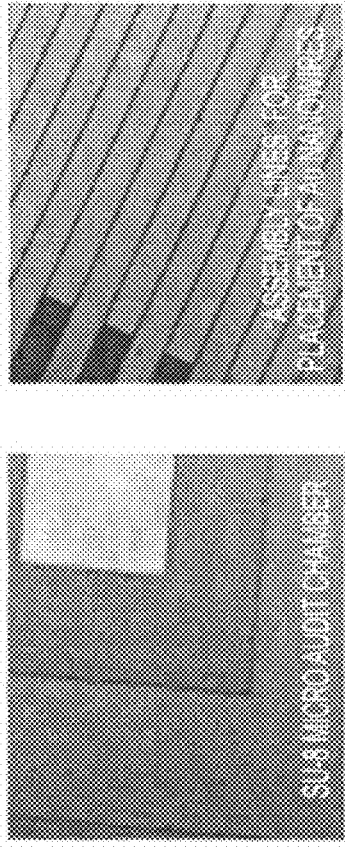
FIG. 16B
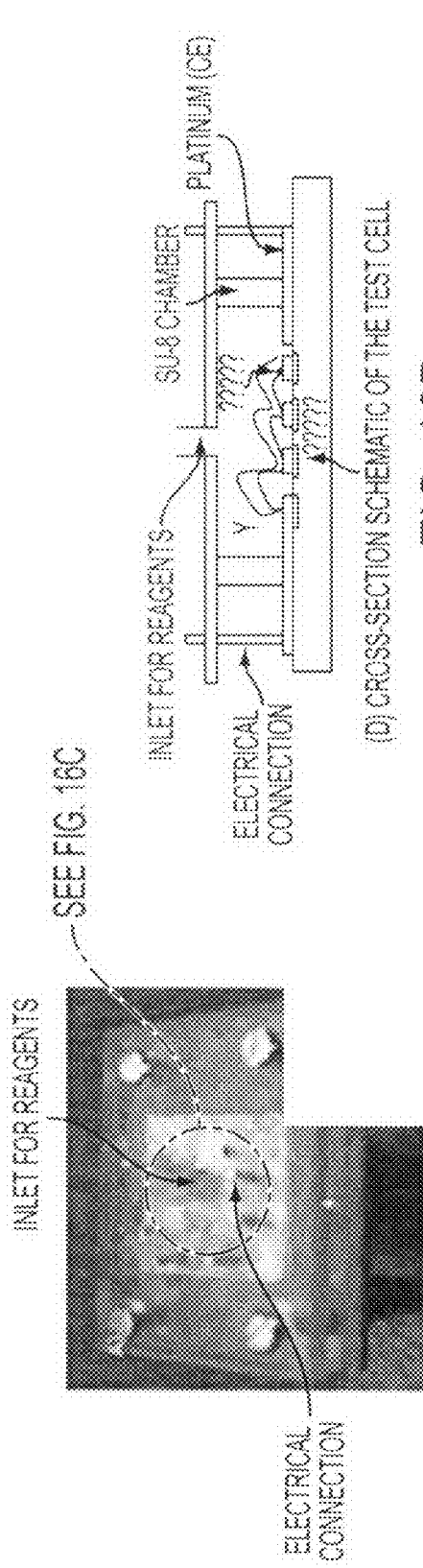
FIG. 16A
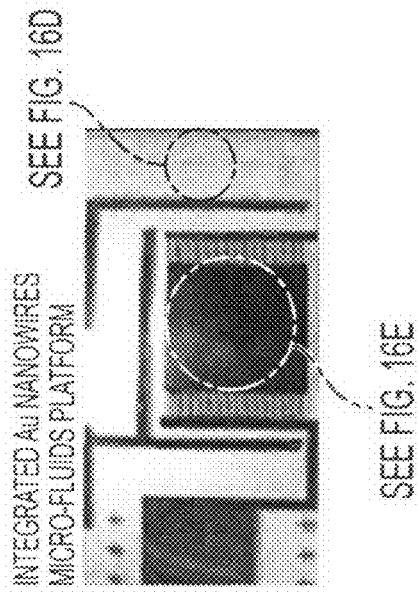
FIG. 16E
FIG. 16D
FIG. 16C

NANO-BASED DEVICE FOR DETECTION OF DISEASE BIOMARKERS AND OTHER TARGET MOLECULES

CROSS-REFERENCE TO RELATED APPLICATIONS

The present application is a continuation-in-part of U.S. application Ser. No. 11/747,125, filed May 10, 2007, which claims the benefit of U.S. Provisional Application Ser. No. 60/814,679, filed Jun. 15, 2006, each of which is hereby incorporated by reference herein in its entirety, including any figures, tables, nucleic acid sequences, amino acid sequences, and drawings.

GOVERNMENT SUPPORT

This invention was made with government support under grant numbers 1R41HL076964-01 and 1R41HL078298-01 awarded by the National Institutes of Health. The government has certain rights in the invention.

BACKGROUND OF THE INVENTION

Cortisol is a steroid hormone produced by the adrenal gland in order to regulate multiple body functions ranging from glucose metabolism to immune function and inflammatory response (Petkus et al., 2006). Cortisol helps to maintain blood pressure, immune function, and the body's anti-inflammatory processes. Aggressive behavior of teenagers can be identified by detecting the cortisol in their saliva sample (Oosterlaan, J. et al., 2005). The amount of cortisol released by the adrenal glands is regulated by the pituitary gland inside the brain. When cortisol levels are low, the pituitary gland secretes the stimulating hormone adrenocorticotropin (ACTH) to prompt the adrenal glands to make more cortisol. High cortisol levels drop when the pituitary gland slows its output of ACTH (Jezova D., 2005).

Cortisone is derived from the peripheral metabolism of cortisol and lacks biological activity. The rapid interconversion between cortisol and cortisone and the altered equilibrium between these steroids may regulate glucocorticoid activity in various tissues. Children with hypoadrenalism exhibited a greater decrease in cortisol as compared with cortisone. Children with adrenal cancer exhibited normal or high values of cortisol, whereas cortisone levels were decreased and the cortisone/cortisol ratio was decreased to nearly zero (Nomura, S. et al., 1996). The simultaneous evaluation of cortisol, cortisone, and the cortisone/cortisol ratio provides a clinical clue of adrenal diseases. Glucocorticoids play an important role in determining body fat distribution, but circulating cortisol concentrations are reported to be normal in obese patients. Conversion of inactive cortisone to active cortisol through the expression of 11beta-hydroxysteroid dehydrogenase type 1 (11betaHSD1) in cultured omental adipose stromal cells; the autocrine production of F may be a crucial factor in the pathogenesis of central obesity (Stewart, P. M. et al., 1999). 11β-Hydroxysteroid dehydrogenase type 2 (11β-HSD2) plays a crucial role in converting hormonally active cortisol to inactive cortisone, thereby conferring specificity on the mineralocorticoid receptor (Marcus Quinkler et al. 2003). The normal ranges observed for cortisol varies from laboratory to laboratory but are usually within the following ranges for blood: adults (8 A.M.): 6-28 mg/dL; adults (4 P.M.): 2-12 mg/dL; child one to six years (8 A.M.): 3-21 mg/dL; child one to six years (4 P.M.): 3-10 mg/dL; newborn: 1/24 mg/dL.

Cortisol detection is performed on patients who may have malfunctioning adrenal glands. Blood and urine cortisol, together with the determination of adrenocorticotropic hormone (ACTH), are the three most important tests in the investigation of Cushing's syndrome (caused by an overproduction of cortisol) and Addison's disease (caused by the underproduction of cortisol). This test is a measure of serum cortisol (also known as hydrocortisone), or urine cortisol, (also known as urinary free cortisol), an important hormone produced by a pair of endocrine glands called the adrenal glands.

Some disorders can be treated with synthesized cortisol, called corticosteroids. One of the main side effects of long term treatment is osteoporosis (thinning of the bones). Levels of cortisol in the body change throughout the day, never being the same. They are highest in the morning, dropping rapidly until mid-day, and gradually declining throughout the rest of the day, being lowest at night (Kurina et al., 2004). Abnormal levels of cortisol may influence certain pathological conditions such as Type 2 Diabetes, constant stress, obesity, metabolic syndrome, etc. It has even been shown that elevated levels of cortisol may be influencing the severity of epileptic seizures since the increase in the adrenocorticotropic hormone as well as cortisol levels has been documented in epileptic postictal period (Galimberti et al., 2005). Since the 1960s, glucocorticoids are used by athletes to improve their performances. Their use is restricted in sports. One of the commonly used tests to determine the cortisol levels is the saliva test (Petkus et al., 2006).

Some of the more common side effects of cortisol-like drugs includes fluid retention (oedema), thin skin, susceptibility to bruising, high or increased blood pressure, osteoporosis (thinning of the bones), bone fractures, particularly in the spine and ribs.

Symptoms of cortisol insufficiency can include: fatigue, nausea and vomiting, low blood pressure, particularly when standing up from a sitting or lying position (orthostatic hypotension), low blood sugar, shock, and coma.

Thus far, the existing methods to detect cortisol, such as the fluorimetric assay (Appel, D. et al. 2005) and reverse phase chromatography (Gatti, R., et al., 2005), are limited with respect to their sensitivity, time of analysis, and cost. Enzyme fragment complementation (EFC) technology provides a sensitive and homogeneous method for measuring analytes by enzymatically amplifying the signal. These fragments are inactive separately but, in solution, they rapidly recombine to form an active enzyme by the process of complementation.

In monitoring medical conditions and the response of patients to efforts to treat medical conditions, it is desirable to use analytical methods that are fast, accurate, and convenient for the patient. Electrochemical methods have been useful for quantifying certain analytes in body fluids, particularly in blood samples. Typically, these analytes undergo oxidation-reduction reactions when in contact with specific enzymes, and the electric current generated by these reactions can be correlated with the concentration of the analyte of interest. Miniaturized versions of analytical electrochemical cells have been developed that allow patients to monitor levels of particular analytes on their own, without the need for a healthcare provider or clinical technician. Typical patient-operated electrochemical sensors utilize a single measuring unit containing the necessary circuitry and output systems. In use, this unit is connected to a disposable analysis strip containing the electrodes and the necessary reagents to measure the electrochemical properties of a sample that is applied to the strip. The most common of these miniature electrochemical systems are the glucose sensors that provide measurements of blood glucose levels. Ideally, a miniature sensor for glucose should provide accurate readings of blood glucose levels by analyzing a single drop of blood, typically from 1-15 microliters (µL).

In a typical analytical electrochemical cell, regardless of the size of the system, the oxidation or reduction half-cell reaction involving the analyte either produces or consumes electrons. This electron flow can be measured, provided the electrons can interact with a working electrode that is in contact with the sample to be analyzed. The electrical circuit is completed through a counter electrode that is also in contact with the sample. A chemical reaction also occurs at the counter electrode, and this reaction is of the opposite type (oxidation or reduction) relative to the type of reaction at the working electrode. See, for example, Fundamentals of Analytical Chemistry, 4th Edition, D. A. Skoog and D. M. West; Philadelphia: Saunders College Publishing (1982), pp 304-341.

The basic components of an electrochemical sensor are a working electrode (also referred to as a sensing electrode, measuring electrode, or anode), a counter electrode (also referred to as a cathode), and usually a reference electrode. These electrodes can be enclosed in a sensor housing in contact with an electrolyte (normally an aqueous solution of strong inorganic acids such as sulfuric or phosphoric acid). When a target molecule is detected, the cell generates a small current proportional to the concentration of the target molecule in the sample. In its simplest form, an electrochemical sensor includes a diffusion barrier, a working electrode, a counter electrode, and an electrolyte. In an environment free of chemically reactive molecules, oxygen diffuses into the cell and adsorbs on both electrodes. The result is a stable potential between the two in which little and, theoretically, no current flows. When a chemically reactive molecule passes through the diffusion barrier it is either oxidized (accepts oxygen and/or gives up electrons) or reduced (gives up oxygen and/or accepts electrons), depending upon the target molecule. The resulting potential difference between the two electrodes causes a current to flow.

The working electrode is typically on the inner face of a diffusion barrier such as a membrane (e.g., Teflon® membrane) that is porous to the target molecule, but impermeable to the electrolyte. The target molecule diffuses into the sensor and through the membrane to the working electrode. When the target molecule reaches the working electrode, an electrochemical reaction occurs; either an oxidation or reduction depending on the type of sample or target molecule.

For example, carbon monoxide may be oxidized to carbon dioxide, or oxygen may be reduced to water. An oxidation reaction results in the flow of electrons from the working electrode to the counter electrode through the external circuit; and conversely a reduction reaction results in flow of electrons from the counter electrode to the working electrode. This flow of electrons constitutes an electric current, which is proportional to the target molecule concentration. When carbon monoxide, a reducing gas, diffuses to the sensing electrode, it is oxidized causing the potential of the sensing electrode to shift in a negative (cathodic) direction. The more modern form of cell utilizes a reference electrode. This electrode has a stable potential from which no current is drawn. It is used to eliminate interference from side reactions with the counter-electrode. In addition, it allows the sensing-electrode potential to be biased with respect to its rest potential. Biasing is one method of controlling sensitivity to a particular target molecule. In order to provide for extended storage, a shorting clip can be connected across the working and reference terminals. This short maintains the electrodes at the same potential and keeps current from flowing through the cell. The electrochemical cell typically includes a casing containing an electrolyte liquid or gel and three electrodes. The top of the casing has a membrane permeable to the target molecule as well as a gas capillary. The electrodes are carefully constructed to provide maximum sensitivity and long life, through a electrode construction which allows more surface area. This allows a larger signal, a quicker response and permits a smaller volume of electrolyte to provide the same life available from large sensors. Each cell is constructed using special filters, electrodes, and electrolytes to make the cell as specific as possible. Electronics should provide appropriate bias current to eliminate interfering sensitivity. Because electrochemical reactions, like all chemical processes, are temperature dependent, electrochemical sensors often incorporate a sensitive temperature sensor which the electronics use to compensate for temperature variations.

The electronics in the instrument detects and amplifies the current and scales the output according to the calibration. The instrument usually displays the target molecule concentration in, for example, parts per million (PPM) for toxic gas sensors and percent volume for oxygen sensors.

There is a need for miniaturized electrochemical systems with improved sensitivity to the concentration of target molecules in samples. It is desirable for miniaturized electrochemical strips to contain independently optimized electrodes having high conductivities.

BRIEF SUMMARY OF THE INVENTION

It was determined by the present inventors that the enzyme fragment complementation (EFC) method may be combined with nanowires to enhance the sensitivity of electrochemical detection of a target molecule (e.g., cortisol). Because of their aligned nature, it was proposed by the inventors that nanowires (e.g., gold nanowires) can improve electron transfer between the functionalized electrodes and interacting substrate due to a large surface-to-volume ratio, small diffusion time, and high electrical conductivity. To test this hypothesis, functionalized gold (Au) nanowires were used for the identification and quantification of endogenous glucocorticoid cortisol as a target molecule. The results demonstrate that the two sets of nanowires used in the sensor platform with the electrochemical technique makes this assay a more economical and easily miniaturized approach for highly sensitive screening for cortisol, and other analytes and disease biomarkers.

The present invention pertains to a nano-based sensing device (also referred to interchangeably herein as the "sensor", "sensor device", "biosensor", or "electrochemical sensor") that can be used for the ultra-sensitive detection of target molecules, including analytes, such as cancer biomarkers and other molecules. The sensor of the invention comprises an electrode system comprising a nano-scale working electrode, a counter electrode, and, optionally, a reference electrode. At least one binding agent capable of binding a target molecule is coupled to the nano-scale working electrode.

The electrode system preferably comprises a nano-scale working electrode, a counter electrode, and a reference electrode; however, it is contemplated that the reference and counter electrodes may be combined in some circumstances, e.g. when the measurement of current is small. Furthermore, optionally, the counter electrode can function as a support for other electrodes such as the working electrode.

Each electrode can be any shape, orientation, or geometry that permits the electrode to function for its intended purpose. For example, the nano-scale working electrode can comprise nano-wires (preferably, aligned), nano-rods, nano-tubes (e.g., carbon nano-tubes), nano-particles, and/or nano-spheres. By the term "nano" or "nano-scale", it is intended that the particular component has at least one dimension (e.g., diameter) that is an average of 100 nm or less.

The selection of materials for each electrode in a particular sensing device can be determined by one skilled in the art. Various metals individually or in combination can be used in the construction of an electrode in order to obtain the intended properties. Examples of such metals include Au, Pt, Ag, Co, Pd, Rh, Ni, Cr, Fe, Mo, Ti, Cu, W and alloys containing two or more of these. Electrode systems for construction of a sensor according to the present invention, preferably comprise noble metals, most preferably the electrode comprises one or more elements selected from the group comprising gold, platinum, radium, palladium, rhenium and carbon.

Other conductive members can be used to transport charge. A material having high conductivity and sufficient electrochemical stability under conditions where the electrode is used can be preferably used as a material forming an electrode. Examples of materials forming such conductive members include metals, conductive polymers, metal oxides and carbon materials, each of which can be used for construction of the electrodes of the invention. Examples of metals include those containing Au, Pt, Ag, Ni, Cr, Fe, Mo, Ti, Al, Cu, V, In, Ga or W, which may be an alloy or may be plated. Examples of conductive polymers include those containing at least one compound selected from the group consisting of polyacetylene, polyarylene, polyarylenevinylene, polyacene, polyarylacetylene, polydiacetylene, polynaphthalene, polypyrrole, polyaniline, polythiophene, polythienylenevinylene, polyazulene and polyisothianaphthene. Examples of metal oxides include those containing at least one element selected from the group consisting of In, Sn, Zn, Ti, Al, Si, Zr, Nb, Mg, Ba, Mo, W, V and Sr. Examples of suitable carbon materials include graphite, carbon black, carbon nanotubes, carbon nanohorns, fullerene compounds and derivatives thereof.

Preferably, the working electrode comprises nano-scale wires composed of gold; however, as indicated above, the working electrode may comprise one or more other materials such as those known in the art for construction of working electrodes. Preferably, the counter electrode comprises platinum; however, as indicated above, the counter electrode may comprise one or more other materials such as those known in the art for construction of counter electrodes. In one embodiment, the counter electrode comprises a conductive metal such as platinum, deposited on a substrate such as a silicon chip. Preferably, the reference electrode comprises silver/silver chloride; however, as indicated above, the reference electrode may comprise one or more other materials such as those known in the art for reference electrodes. Preferably, the binding agent is an antibody or antibody fragment immunospecific for the target molecule to be detected.

The electrochemical sensor and methods of the invention can be utilized in research and various industries, such as medical diagnostics, environmental management (e.g., detection of contaminants in water and wastewater treatment systems), bioremediation, public health, and homeland security (e.g., detection of bioterrorism agents).

In one embodiment, the sensor of the invention is a cortisol/cholesterol sensor based on functionalized gold nanowires utilizing EFC technology. In one embodiment, the method of the invention is a cortisol/total cholesterol detection assay that utilizes the cortical/cholesterol sensor of the invention.

The sensor described in the Examples was fabricated using aligned, gold (Au) nanowire as a working electrode, platinum nanowires as a counter electrode, and silver/silver chloride nanowires as a reference electrode, which are deposited on a silicon wafer. The gold nanowires are coupled with cortisol antibodies and 3α-hydroxysteroid dehydrogenase using covalent linkage. In those embodiments in which 3α-hydroxysteroid dehydrogenase is immobilized on the working electrode, it is preferred that the human enzyme is used (see, for example, Khanna M. et al., *J. Biol., Chem.*, 1995, 270(34): 20162-20168, and NCBI Accession No. AAB41916, which are incorporated herein in their entirety. However, enzymes from other animals (e.g., mammals) or microorganisms may also be used (see, for example, NCBI Accession Nos. AAC45414, and AAB21513, and Pawlowski J. et al., *Agents Actions*, 1991, 34(1-2):289-293, which are incorporated herein by reference in their entirety).

Preferably, the sensor is further equipped with a microfluid system which can be fabricated with micro electromechanical system (MEMS) technology to have better control on liquid flow over the electrodes.

Without being limited by a particular theory or mechanistic scheme, the expected advantage in using the nanowires is to enhance the sensitivity of the sensor due to improved electron transfer between the functionalized electrodes and interacting substrate. This is possible due to their large surface-to-volume ratio, small diffusion time, and high electrical conductivity because of their aligned nature. This sensor is further characterized using SEM, AFM and FTIR techniques and its curve is linear from 10 nM to 80 nM concentration of cortisol. Moreover, the presence of the hydrocortisone is sensitively detected in the range of 5 nM to 30 nM and. The modified Au nanowires showed a stable calibration line and a quasi-linear relationship between cholesterol level and current response in the range of 0-6 mM (over the baseline blood cholesterol level). The sensitivity of the modified electrode was found to be about 0.74 μA/mM.

BRIEF DESCRIPTION OF THE DRAWINGS

FIGS. 4A-D show an electrochemical test set up, seen with the silicon chip, inlet for reagents and electrical connections (FIG. 4A), an image of the micro-fluidic platform in silicon with electrodes and SU-8 chamber (FIG. 4B), an image of the platinum "assembly" lines for nanowire alignment (FIG. 4C), and an image of the hard-baked SU-8 micro-fluidic chamber (FIG. 4D).

FIGS. 16A-16E show A) the electrochemical test set up, seen with the silicon chip, inlet for reagents and electrical connections; B) a schematic of the test cell in cross-section; C) actual image of the micro-fluidic platform in silicon with electrodes and SU-8 chamber; D) image of the platinum "assembly" lines for working electrode (nano-wire) alignment; and E) image of the hard-baked SU-9 micro-fluidic chamber. FIGS. 4 and 16A-E correspond to FIG. 2 of Kumar et al., *Biosens. Bioelectron.*, 2007, 22(9-10):2138-2144, which is incorporated herein by reference in its entirety.

DETAILED DESCRIPTION OF THE INVENTION

Figure 1:
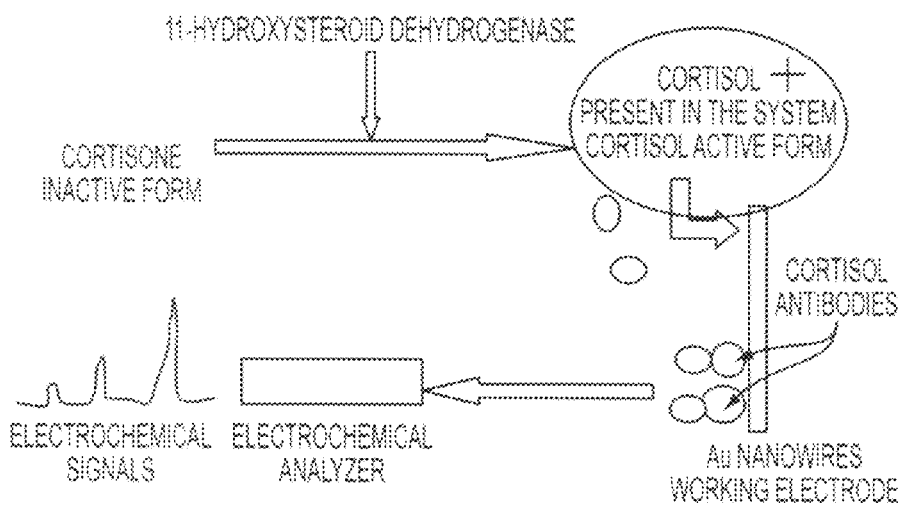
FIG. 1 shows a schematic of the cortisol detection scheme used by an embodiment of the invention.

As described in the background section, conventional electrochemical systems having three electrodes typically employ (1) a working electrode, (2) a reference electrode, and (3) a counter electrode. The reaction at the working electrode is monitored and controlled. The functions of the reference and counter electrodes ensure that the working electrode actually experiences the desired conditions, i.e., the correct potential to be applied. The reference electrode measures the potential at the interface of the working electrode and the sample as accurately as possible. In an ideal situation, no current passes through the reference electrode. The counter electrode ensures that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential applied between the counter electrode and working electrode is altered accordingly, i.e., the potential is either increased or decreased. The reaction at the counter electrode is also equal and opposite to the charge transfer reaction occurring at the working electrode, i.e., if an oxidation reaction is occurring at the working electrode then a reduction reaction will take place at the counter electrode, thereby allowing the sample to remain electrically neutral.

The present invention pertains to a nanowire-based microfluidic electrochemical sensor that can be used for the ultrasensitive detection of target molecules including analytes, such as cancer biomarkers and other chemical entities, in a medium such as a biological or environmental sample. In one embodiment, the sensor of the invention comprises an electrode system comprising a working electrode, a counter electrode, and, optionally, a reference electrode; and a solid support. Preferably, the solid support comprises an electrically non-conductive surface.

Some embodiments of the sensor device of the invention are described in Kumar, A. et al., "Ultrasensitive detection of cortisol with enzyme fragment complementation technology using functionalized nanowire", *Biosens. Bioelectron.*, 2007, 22(9-10):2138-2144, Epub Nov. 9, 2006; and Aravamudhan, S. et al., "Sensitive estimation of total cholesterol in blood using Au nanowires based micro-fluidic platform", *Biosens. Bioelectron.*, 2007, 22(9-10):2289-2294, Epub Jan. 9, 2007, which are each incorporated herein by reference in their entirety.

Preferred embodiments of the sensor comprise a nanoscale working electrode comprising a conductive material such as aligned gold (Au) nanowires; a counter electrode comprising a conductive material, such as platinum deposited on a substrate (e.g., silicon chip or wafer); and a reference electrode comprising a conductive materials such as silver/silver chloride. Preferably, the working electrode is coupled (e.g., coated) with a binding agent such as antibodies or antibody fragments that bind to the target molecule of interest (e.g., disease biomarker, antigen, or other molecule). The antibodies can be coupled to the working electrode using covalent linkage, for example. Preferably, the sensor further comprises a sample loading area. Preferably, the sensor is further equipped with a micro-fluidic chip that can be fabricated using micro electromechanical system (MEMS) technology to have better control on liquid flow over the working electrode.

Optionally, the sensor further comprises an enzyme coupled to the working electrode, wherein the enzyme acts on a substrate that is an alternative form of the target molecule to thereby produce the target molecule. For example, in one embodiment, the enzyme is hydroxysteroid dehydrogenase, the substrate is cortisone, and the target molecule is cortisol.

In addition to the sensor (sensor element) of the invention, devices of the invention can comprise one or more other components typical of microfluidic chip apparatus, such as microfluid chip, sample inlet ports and/or outlet ports, Pogo pins, fluid interconnects (preferably with self-sealing gaskets), filter material for separating components of a sample (examples of suitable filter material include synthetic membranes, nitrocellulose, cellulose, silica, filter paper and agar gel), and transparent top cover plates (providing optical access). Optionally, the solid support (e.g., silicon substrate) includes "assembly" lines bridged by the nano-scale working electrode (e.g., aligned nanowires).

In some embodiments, the sensor of the invention utilizes enzyme fragment complementarity (EFC) to enzymatically amplify signal. EFC is a generic term to describe the combination of enzyme fragments to form active enzyme, followed by detection of that activity, e.g., by measurement of a hydrolysis product, typically by calorimetric, fluorometric or chemiluminescent methods. EFC has the advantage of providing an amplification step, due to enzyme turnover, as part of the detection system.

Another aspect of the invention concerns a method for detecting a target molecule in a medium, such as a sample, comprising contacting a sensor of the invention with the medium under conditions sufficient for the target molecule(s) to be detected, if present. Preferably, the concentration of the target molecule(s) is determined.

The sensor and detection methods of the invention may be utilized in research and various industries, such as environmental management (e.g., water and wastewater treatment systems), bioremediation (e.g., to determine optimum conditions for microbial growth), public health (e.g., identification of rapidly growing infectious microbes), and homeland security (e.g., identification of rapidly growing bioterrorism agents).

Optionally, the sensor of the invention includes an output device in communication with the sensing element of the sensor. An indication of a target molecule's presence or a detected molecule's concentration can be displayed on the output device, such as an analog recorder, teletype machine, typewriter, facsimile recorder, cathode ray tube display, computer monitor, or other computation device. Optionally, in addition to the displayed presence of the target molecule or the concentration of the target molecule, the output device displays the conditions under which the detection was carried out (such as temperature).

Optionally, in the various embodiments of the invention, the detecting method further comprises comparing the concentration of the target molecule in the medium (e.g., a bodily fluid), as determined above, to pre-existing data characterizing the medium (e.g., concentration of the same target molecule in the same patient or a different patient). The target molecule concentration may be that specific target molecule concentration observed under particular conditions.

Optionally, the detecting method of the invention further comprises monitoring the presence and/or concentration of one or more target molecules in a medium over a period of time.

Ex vivo analysis of bodily fluids utilizing methods disclosed herein can be applied to a wide range of diagnostic tests. For example, potential applications include detection of licit and illicit drugs, detection of a wide range of biomarkers related to specific diseases, and detection of any other compounds that appear in bodily fluids. These tests can be highly quantitative because of the sensor's sensitivity. Moreover, analysis of bodily fluid samples using the method of the present invention can enable timely interventions for time-sensitive conditions or diseases.

In one embodiment, the sensor of the invention is a cortisol/cholesterol sensor based on functionalized gold nanowires utilizing EFC technology. In one embodiment, the method of the invention is a cortisol/total cholesterol detection assay that utilizes the cortical/cholesterol sensor of the invention. Cortisol is a member of the glucocorticoid hormone family, and is a key metabolic regulator. Increased intracellular cortisol levels have been implicated in Type 2 diabetes, obesity, and metabolic syndrome. Cortisol is important an bio-marker of stress and its detection is important in sports medicine. However, available methods for rapidly and sensitively detecting cortisol are limited. It was reasoned by the present inventors that Au nanowires may enhance the sensitivity of the device due to improved electron transfer between the functionalized electrodes and interacting substrate because of large surface-to-volume ratio, small diffusion time, and high electrical conductivity because of their aligned nature. To test this hypothesis, a biosensor was fabricated using, aligned gold (Au) nanowires as a working electrode, platinum deposited on a silicon chip as a counter electrode, and silver/silver chloride as a reference electrode. The gold nanowires were coupled with cortisol antibodies and 3α-Hydroxysteroid dehydrogenase using covalent linkage. This device was further equipped with a micro-fluidic chip which is fabricated with the help of MEMS technology to have better control on liquid flow over Au nanowires. This device was further characterized using SEM, AFM, and FTIR techniques. As described in the Examples, analysis of detection capability with diluting doses showed a standard in the linear range between 10 μM to 80 μM concentration of cortisol. Moreover, the presence of the hydrocortisone is sensitively detected in the range of 5 μM to 30 μM. It is concluded that the enzyme fragment complementation technology using functionalized gold nanowires can provide an assay for cortisol detection.

11β-Hydroxysteroid dehydrogenase type 1 (11β-HSD1) inter-converts inactive cortisone and active cortisol to enhance the signal remarkable event in the small sample size. The rate of conversion of cortisone into cortisol in the presence of 11-Hydroxysteroid dehydrogenase provides important information as to the total cortisol present in the system. Moreover, cortisol concentration depends on the amount of 3α-Hydroxysteroid dehydrogenase present in the system. Another advantage of the detection scheme used by the invention is that the inactive form and active form can be detected sensitively by the inter-conversion technology that is used in the present approach. The combination of Au nanowires coupled with monoclonal antibodies of cortisol remarkably improves the sensitivity of the sensor. The biosensor is found to be sensitive enough in the desired physiological range. The micro-fluidic chip has added advantages, such as the control over the flow of liquid over the nanowire electrode, which makes it more stable.

Some of the conditions treated with cortisol-like drugs include skin disorders, and in organ transplant surgery, cortisol-like drugs are used to inhibit the body's immune response so that a transplanted organ is not rejected. Since cortisol acts on so many organs and tissues of the body, several unwanted side effects can occur during treatment with cortisol-like drugs. It is anticipated that the Au nanowires can be used in an electrochemical method to readily detect cortisol in a non-invasive way.

The sensor of the present invention can provide signals indicative of the presence of a target molecule and, preferably, target molecule concentration within a medium, such as a biological fluid.

Due to its increased sensitivity, use of the sensor of the invention in vitro or in vivo can facilitate medical diagnoses at the doctor's office and/or at the bedside of the patient.

The sensor of the present invention can be constructed in any form adapted for the intended use. Thus, sensors intended for repeated laboratory use can be constructed in the form of an elongated probe having the sensor element itself located at one end and electrical conductors connecting the electrode system of the sensing element to points of electrical attachment of the probe sensor to a programmable sensor controller. In another embodiment, the sensor can be constructed using art recognized micro-scale manufacturing techniques to produce needle-like sensors capable of being implanted or injected into an anatomical site for indwelling sensor applications.

The contacting step in the assays (methods) of the invention can involve combining or mixing the sample and the sensor of the invention in a suitable receptacle, such as a reaction vessel, microvessel, tube, microtube, well, or other solid support. Samples and/or sensors of the invention may be arrayed on a solid support, such as a multi-well plate. "Arraying" refers to the act of organizing or arranging members of a library (e.g., an array of different samples or an array of sensors that target the same analyte or different analytes), or other collection, into a logical or physical array. Thus, an "array" refers to a physical or logical arrangement of, e.g., library members (candidate agent libraries). A physical array can be any "spatial format" or physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multiwell plate. Similarly, sensors can be plated or otherwise deposited in microtitered, e.g., 96-well, 384-well, or -1536 well, plates (or trays). Optionally, sensors may be immobilized on the solid support.

Detection of analytes and other assays carried out on samples can be carried out simultaneously or sequentially with detection of other target molecules, and may be carried out in an automated fashion, in a high-throughput format.

Antibodies

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region. Native antibodies and immunoglobulins are usually heterotetrameric glycoproteins of about 150, 000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.,* 1985, 186:651-666; Novotny and Haber, *Proc. Natl. Acad. Sci. USA,* 1985, 82:4592-4596).

The antibodies that are coupled (e.g., covalently) to the nanowires of the working electrode can be monoclonal antibodies, polyclonal antibodies, phage-displayed mono-specific antibodies, etc. Preferably, the antibodies specifically bind to, or are immunospecific for, ligands that are part of, or attached to, a target molecule of interest. Antibodies for detection of many target molecules of interest are commercially available, or can be conveniently produced from available hybridomas, for example. Additionally, specific antibodies can be produced de novo using phage display or other protein engineering and expression technologies. Different antibodies that bind to different target molecules can be utilized in a sensor of the invention. For example, two or more types of antibodies or antibody fragments can be coupled (e.g., immobilized) to the working electrode, with each antibody or antibody fragment having affinity for an entirely unrelated target molecules, or having affinity for related molecules. For example, a first antibody or antibody fragment can exhibit affinity for a target molecule and a second antibody or antibody fragment can exhibit affinity for a related target molecule. In one embodiment, the related target molecules are different forms of the same molecule. For example, one target molecule can be an active form of a molecule and the other target molecule can be an inactive form of the molecule.

An antibody that is contemplated for use in the present invention can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. The present invention contemplates the use of any specificity of an antibody, polyclonal or monoclonal, and is not limited to antibodies that recognize and immunoreact with a specific antigen.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments can retain an ability to selectively bind with the antigen or analyte and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269 315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., *Proc. Natl. Acad. Sci. USA,* 1993, 90: 6444-6448.

The preparation of polyclonal antibodies is well known to those skilled in the art. See, for example, Green, et al., Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1 (1992), which are hereby incorporated by reference.

The preparation of monoclonal antibodies likewise is conventional. See, for example, Kohler & Milstein, *Nature*, 1975, 256:495; Coligan et al., sections 2.5.1 2.6.7; and Harlow, et al., in: Antibodies: A Laboratory Manual, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1 2.7.12 and sections 2.9.1 2.9.3; Barnes, et al., Purification of Immunoglobulin G (IgG), in: Methods in Molecular Biology, Vol. 10, pages 79 104 (Humana Press, 1992).

The term "monoclonal antibody", as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., *Proc. Natl. Acad. Sci.*, 1984, 81:6851-6855.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, *Nature*, 1975, 256:495, or may be made by recombinant methods, e.g., as described in U.S. Pat. No. 4,816,567. The monoclonal antibodies for use with the present invention may also be isolated from phage antibody libraries using the techniques described in Clackson et al, *Nature*, 1991, 352:624-628, as well as in Marks et al., *J. Mol Biol.*, 1991, 222:581-597. Another method involves humanizing a monoclonal antibody by recombinant means to generate antibodies containing human specific and recognizable sequences. See, for review, Holmes, et al., *J. Immunol.*, 1997, 158:2192-2201 and Vaswani, et al., *Annals Allergy, Asthma & Immunol.*, 1998, 81:105-115.

Methods of making antibody fragments are also known in the art (see for example, Harlow and Lane, Antibodies: A Laboratory Manual, Cold Spring Harbor Laboratory, New York, (1988), incorporated herein by reference). Antibody fragments can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab monovalent fragments. Alternatively, an enzymatic cleavage using pepsin produces two monovalent Fab fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing sFvs are described, for example, by Whitlow, et al., Methods: a Companion to Methods in Enzymology, Vol. 2, page 97 (1991); Bird, et al., *Science*, 1988, 242:423 426; Ladner et al., U.S. Pat. No. 4,946,778; and Pack, et al., *Bio/Technology*, 1993, 11:1271-1277.

Another form of an antibody fragment that may be used in the present invention is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, 1991, Vol. 2, page 106.

Human and humanized forms of non-human (e.g., murine) antibodies may be used in the sensor and methods of the present invention. Such humanized antibodies are chimeric immunoglobulins, immunoglobulin chains or fragments thereof (such as Fv, Fab, Fab', $F(ab')_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies can comprise substantially all of at least one, and typically two, variable domains, in which all or substantially all of the CDR regions correspond to those of a non-human immunoglobulin and all or substantially all of the Fv regions are those of a human immunoglobulin consensus sequence. The humanized antibody optimally also will comprise at least a portion of an immunoglobulin constant region (Fc), typically that of a human immunoglobulin. For further details, see: Jones et al., *Nature*, 1986, 321: 522-525; Reichmann et al., *Nature*, 1988, 332:323-329; Presta, *Curr. Op. Struct. Biol.*, 1992, 2:593-596; Holmes, et al., *J. Immunol.*, 1997, 158:2192-2201, and Vaswani et al., *Annals Allergy, Asthma & Immunol.*, 1998, 81:105-115.

The binding agents (e.g., antibodies or antibody fragments) can include a detectable label (e.g., a detectable moiety) indicating when binding to the target molecule has occurred. Examples of labels include optical labels and fluorescent labels (e.g., immunofluorescence). Other examples of labels include, but are not limited to, the following radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkalline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Methods for conjugating or labeling the antibodies discussed above may be readily accomplished by one of ordinary skill in the art. (See, for example, Imman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988, regarding methods for conjugating or labeling the antibodies with an enzyme or ligand binding partner). Time-resolved fluorometry may be used to detect a signal. For example, the method described in Christopoulos T. K. and Diamandis E. P., *Anal. Chem.*, 1992:64:342-346 may be used with a conventional time-resolved fluorometer. Examples of enzymes and substrates for enzymes that provide such fluorescent complexes are described in U.S. Pat. No. 5,3112,922 to Diamandis. By way of example, when the antibody is directly or indirectly labeled with alkalline phosphatase, the substrate employed in the method may be 4-methylumbeliferyl phosphate, or 5-fluorpsalicyl phosphate. The fluorescence intensity of the complexes is typically measured using a time-resolved fluorometer, e.g., a CyberFluor 615 Immoanalyzer (Nordion International, Kanata Ontario).

However, in preferred embodiments, instead of a label, a signal (electric current) is sent to an electrochemical analyzer, as shown in FIG. 1. Typically, use of an electrochemical analyzer will increase the sensitivity of the sensor. Thus, some embodiments of the sensing device of the invention include an electrochemical analyzer connected to the electrode system of the device.

Binding agents other than antibodies may be utilized, so long as there exists a molecular binding partner or specific binding partner (i.e., binding agent and corresponding analyte) for the target molecule of interest. Molecular binding partners include, for example, receptor and ligand, antibody and antigen, biotin and avidin, and biotin and streptavidin.

Microfluidic Systems

The devices of the invention may allow a broad range of assays, such as drug screens, cell characterizations, research studies, and/or clinical analyses, among others, to be scaled down to microfluidic size. Such assays may use less sample and reagent, may be less labor intensive, and/or may be more informative than comparable macrofluidic assays.

Detection methods of the invention can be performed using microfluidic systems (also referred to herein as a microfluid or microfluidic platform). A microfluidic system generally comprises any system in which very small volumes of fluid are stored and manipulated, generally less than about 500 µL, typically less than about 100 µL, and more typically less than about 10 µL. Microfluidic systems carry fluid in predefined paths through one or more microfluidic passages. A microfluidic passage may have a minimum dimension, generally height or width, of less than about 200, 100, or 50 µm. Passages are described in more detail below.

Microfluidic systems may include one or more sets of passages that interconnect to form a generally closed microfluidic network. Such a microfluidic network may include one, two, or more openings at network termini, or intermediate to the network, that interface with the external world. Such openings may receive, store, and/or dispense fluid. Dispensing fluid may be directly into the microfluidic network or to sites external to the microfluidic system. Such openings generally function in input and/or output mechanisms, and may include reservoirs, described in more detail below.

Microfluidic systems also may include any other suitable features or mechanisms that contribute to fluid, reagent, and/or sample analysis. For example, microfluidic systems may include regulatory or control mechanisms that determine aspects of fluid flow rate and/or path. Valves and/or pumps that may participate in such regulatory mechanisms are described in more detail below. Alternatively, or in addition, microfluidic systems may include mechanisms that determine, regulate, and/or sense fluid temperature, fluid pressure, fluid flow rate, exposure to light, exposure to electric fields, magnetic field strength, and/or the like. Accordingly, microfluidic systems may include heaters, coolers, electrodes, lenses, gratings, light sources, pressure sensors, pressure transducers, microprocessors, microelectronics, and/or so on. Furthermore, each microfluidic system may include one or more features that act as a code to identify a given system. The features may include any detectable shape or symbol, or set of shapes or symbols, such as black-and-white or colored barcode, a word, a number, and/or the like, that has a distinctive position, identity, and/or other property (such as optical property).

Microfluidic systems may be formed of any suitable material or combination of suitable materials. Suitable materials may include elastomers, such as polydimethylsiloxane (PDMS); plastics, such as polystyrene, polypropylene, polycarbonate, etc.; glass; ceramics; sol-gels; silicon and/or other metalloids; metals or metal oxides; biological polymers, mixtures, and/or particles, such as proteins (gelatin, polylysine, serum albumin, collagen, etc.), nucleic acids, microorganisms, etc.

Microfluidic systems, also referred to as chips, may have any suitable structure. Such systems may be fabricated as a unitary structure from a single component, or as a multi-component structure of two or more components. The two or more components may have any suitable relative spatial relationship and may be attached to one another by any suitable bonding mechanism.

In some embodiments, two or more of the components may be fabricated as relatively thin layers, which may be disposed face-to-face. The relatively thin layers may have distinct thickness, based on function. For example, the thickness of some layers may be about 10 to 250 µm, 20 to 200 µm, or about 50 to 150 µm, among others. Other layers may be substantially thicker, in some cases providing mechanical strength to the system. The thicknesses of such other layers may be about 0.25 to 2 cm, 0.4 to 1.5 cm, or 0.5 to 1 cm, among others. One or more additional layers may be a substantially planar layer that functions as a substrate layer, in some cases contributing a floor portion to some or all microfluidic passages.

Components of a microfluidic system may be fabricated by any suitable mechanism, based on the desired application for the system and on materials used in fabrication. For example, one or more components may be molded, stamped, and/or embossed using a suitable mold. Such a mold may be formed of any suitable material by micromachining, etching, soft lithography, material deposition, cutting, and/or punching, among others. Alternatively, or in addition, components of a microfluidic system may be fabricated without a mold by etching, micromachining, cutting, punching, and/or material deposition.

Microfluidic components may be fabricated separately, joined, and further modified as appropriate. For example, when fabricated as distinct layers, microfluidic components may be bonded, generally face-to-face. These separate components may be surface-treated, for example, with reactive chemicals to modify surface chemistry, with particle binding agents, with reagents to facilitate analysis, and/or so on. Such surface-treatment may be localized to discrete portions of the surface or may be relatively non-localized. In some embodiments, separate layers may be fabricated and then punched and/or cut to produce additional structure. Such punching and/or cutting may be performed before and/or after distinct components have been joined.

Microfluidic systems may include any suitable structure(s) for the integrated manipulation of small volumes of fluid, including moving and/or storing fluid, and particles associated therewith, for use in particle assays. The structures may include passages, reservoirs, and/or regulators, among others.

Passages generally comprise any suitable path, channel, or duct through, over, or along which materials (e.g., fluid, sample, and/or reagents) may pass in a microfluidic system. Collectively, a set of fluidically communicating passages, generally in the form of channels, may be referred to as a microfluidic network. In some cases, passages may be described as having surfaces that form a floor, a roof, and walls. Passages may have any suitable dimensions and geometry, including width, height, length, and/or cross-sectional profile, among others, and may follow any suitable path, including linear, circular, and/or curvilinear, among others. Passages also may have any suitable surface contours, including recesses, protrusions, and/or apertures, and may have any suitable surface chemistry or permeability at any appropriate position within a channel. Suitable surface chemistry may include surface modification, by addition and/or treatment with a chemical and/or reagent, before, during, and/or after passage formation.

In some cases, passages, and particularly channels, may be described according to function. For example, passages may be described according to direction of material flow in a particular application, relationship to a particular reference structure, and/or type of material carried. Accordingly, passages may be inlet passages (or channels), which generally carry materials to a site, and outlet passages (or channels), which generally carry materials from a site. In addition, passages may be referred to as particle passages (or channels), reagent passages (or channels), focusing passages (or channels), perfusion passages (or channels), waste passages (or channels), and/or the like.

Passages may branch, join, and/or dead-end to form any suitable microfluidic network. Accordingly, passages may function in particle positioning, sorting, retention, treatment, detection, propagation, storage, mixing, and/or release, among others.

Reservoirs generally comprise any suitable receptacle or chamber for storing materials (e.g., fluid, particles and/or reagents), before, during, between, and/or after processing operations (e.g., detection, measurement, and/or treatment). Reservoirs, also referred to as wells, may include input, intermediate, and/or output reservoirs. Input reservoirs may store materials (e.g., fluid, sample, and/or reagents) prior to inputting the materials to a microfluidic network(s) portion of a chip. By contrast, intermediate reservoirs may store materials during and/or between processing operations. Finally, output reservoirs may store materials prior to outputting from the chip, for example, to an external processor or waste, or prior to disposal of the chip.

Regulators generally comprise any suitable mechanism for generating and/or regulating movement of materials (e.g., fluid, sample, and/or reagents). Suitable regulators may include valves, pumps, and/or electrodes, among others. Regulators may operate by actively promoting flow and/or by restricting active or passive flow. Suitable functions mediated by regulators may include mixing, sorting, connection (or isolation) of fluidic networks, and/or the like.

Microfluidic systems may include one or more input mechanisms that interface with the microfluidic network(s). An input mechanism generally comprises any suitable mechanism for inputting material(s) (e.g., sample, fluid, and/or reagents) to a microfluidic network of a microfluidic chip, including selective (that is, component-by-component) and/or bulk mechanisms.

The input mechanism may receive material from internal sources, that is, reservoirs that are included in a microfluidic chip, and/or external sources, that is, reservoirs that are separate from, or external to, the chip.

Input mechanisms that input materials from internal sources may use any suitable receptacle to store and dispense the materials. Suitable receptacles may include a void formed in the chip. Such voids may be directly accessible from outside the chip, for example, through a hole extending from fluidic communication with a fluid network to an external surface of the chip, such as the top surface. The receptacles may have a fluid capacity that is relatively large compared to the fluid capacity of the fluid network, so that they are not quickly exhausted. For example, the fluid capacity may be at least about 1, 5, 10, 25, 50, or 100 µL. Accordingly, materials may be dispensed into the receptacles using standard laboratory equipment, if desired, such as micropipettes, syringes, and the like.

Input mechanisms that input materials from external sources also may use any suitable receptacle and mechanism to store and dispense the materials. However, if the external sources input materials directly into the fluid network, the external sources may need to interface effectively with the fluid network, for example, using contact and/or noncontact dispensing mechanisms. Accordingly, input mechanisms from external sources may use capillaries or needles to direct fluid precisely into the fluid network. Alternatively, or in addition, input mechanisms from external sources may use a noncontact dispensing mechanism, such as "spitting," which may be comparable to the action of an inkjet printer. Furthermore, input mechanisms from external sources may use ballistic propulsion of particles, for example, as mediated by a gene gun.

The inputting of materials into the microfluidics system may be facilitated and/or regulated using any suitable facilitating mechanism. Such facilitating mechanisms may include gravity flow, for example, when an input reservoir has greater height of fluid than an output reservoir. Facilitating mechanisms also may include positive pressure to push materials into the fluidic network, such as mechanical or gas pressure, or centrifugal force; negative pressure at an output mechanism to draw fluid toward the output mechanism; and/or a positioning mechanism acting within the fluid network. The positioning mechanism may include a pump and/or an electrokinetic mechanism. In some embodiments, the facilitating mechanism may include a suspension mechanism to maintain particles such as cells in suspension prior to inputting.

DEFINITIONS

As used herein, the term "working electrode" refers to an electrode at which a target molecule is electrooxidized or electroreduced with or without the agency of a redox mediator. The working electrode of the invention is a nano-scale electrode (having at least one dimension that is an average of 100 nm or less), such as aligned nano-wires, nano-rods, nano-tubes (e.g., carbon nano-tubes), nano-particles, nano-spheres, or a combination of any of the foregoing. The electrodes of the invention can be coated with an electrically conductive material.

As used herein, the term "counter electrode" refers to an electrode, used in conjunction with a working electrode, through which passes an electrochemical current equal in magnitude and opposite in sign to the current passed through the working electrode. The term "counter electrode" is meant to include counter electrodes which also function as reference electrodes (i.e., a counter/reference electrode). Optionally, the counter electrode can be arranged on the device so as to function as a support for the working electrode.

The terms "electrochemical sensor", "electrochemical sensor strip", and variations thereof, refer to a device configured to detect the presence of and/or measure the concentration of an analyte via electrochemical oxidation and reduction reactions. These reactions are transduced to an electrical signal that may be correlated to an amount or concentration of target molecule such as a disease biomarker or other analyte.

"Electrolysis" is the electrooxidation or electroreduction of a compound either directly at an electrode or via one or more electron transfer agents (e.g., redox mediators and/or enzymes).

The term "facing electrodes" refers to a configuration of the working and counter electrodes in which the working surface of the working electrode is disposed in approximate opposition to a surface of the counter electrode. The sensor of the invention can comprise facing electrodes.

An "indicator electrode" includes one or more electrodes that detect partial or complete filling of a sample chamber and/or measurement zone. The sensor device of the invention can include an indicator electrode.

The term "planar electrodes" of "co-planar electrodes" refers to a configuration of the working and counter electrodes in which the working surface of the working electrode is disposed at least approximately planar to a surface of the counter electrode. "Planar electrodes" or "co-planar electrodes" are typically located on the same substrate. The electrodes of the invention can be planar electrodes.

A "reference electrode" includes a reference electrode that also functions as a counter electrode (i.e., a counter/reference electrode) unless the description provides that a "reference electrode" excludes a counter/reference electrode.

"Sputter", "sputtering" and variations thereof, includes deposition processes such as vacuum deposition, vapor deposition, thin film deposition, and the like. Sputtering methods may be used to prepare the electrodes in the sensor of the invention.

As used herein, the terms "analyte" and "target molecule" refer to any component (molecular species) of a sample that is desired to be detected, or its influence or interaction detected or measured. The term can refer to a single component or a plurality of components in the sample. As used herein, "analytes" and "biomarkers" are used interchangeably (i.e., "analyte/biomarker") to refer to naturally occurring and/or synthetic compounds that can be found in a biological sample, which are a marker of a condition (e.g., drug abuse), disease state (e.g., infectious diseases), disorder (e.g., neurological disorder, inflammatory disorder, or metabolic disorder), or a normal or pathologic process that occurs in a patient (e.g., drug metabolism). The term "analyte" or "biomarker," as used herein, can refer to any substance, including chemical and/or biological agents that can be measured in an analytical procedure.

Analytes/biomarkers that can be detected using the present invention include, but are not limited to, the following metabolites or compounds commonly found in bodily fluids: acetaldehyde (source: ethanol; diagnosis: intoxication), acetone (source: acetoacetate; diagnosis: diet or ketogenic/diabetes), ammonia (source: deamination of amino acids; diagnosis: uremia and liver disease), CO (carbon monoxide) (source: $CH_2Cl_2$, elevated % COHb; diagnosis: indoor air pollution); chloroform (source: halogenated compounds), dichlorobenzene (source: halogenated compounds), diethylamine (source: choline; diagnosis: intestinal bacterial overgrowth); H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), $Me_2S$ (source: infection; diagnosis trench mouth), alpha II-spectrin breakdown products and/or isoprostanes (source: cerebral spinal fluid, blood; diagnosis: traumatic or other brain injuries); prostate specific antigen (source: prostate cells; diagnosis: prostate cancer); and GLXA (source: glycolipid in *Chlamydia*; diagnosis: *Chlamydia*).

Additional analytes/biomarkers that can be detected using the sensor and methods of the present invention include, but are not limited to, illicit, illegal, and/or controlled substances including drugs of abuse (e.g., amphetamines, analgesics, barbiturates, club drugs, cocaine, crack cocaine, depressants, designer drugs, ecstasy, Gamma Hydroxy Butyrate—GHB, hallucinogens, heroin/morphine, inhalants, ketamine, lysergic acid diethylamide—LSD, marijuana, methamphetamines, opiates/narcotics, phencyclidine—PCP, prescription drugs, psychedelics, Rohypnol, steroids, and stimulants); allergens (e.g., pollen, mold, spores, dander, peanuts, eggs, and shellfish); toxins (e.g., mercury, lead, other heavy metals, and *Clostridium Difficile* toxin); carcinogens (e.g., acetaldehyde, beryllium compounds, chromium, dichlroodiphenyl-trichloroethane (DDT), estrogens, N-methyl-N'-nitro-N-nitrosoguanidine (MNNG), and radon); and infectious agents (e.g., Bordettella bronchiseptica, citrobacter, *Escherichia coli*, hepatitis viruses, herpes, immunodeficiency viruses, influenza virus, *listeria, micrococcus*, mycobacterium, rabies virus, rhinovirus, rubella virus, *Salmonella*, and yellow fever virus).

As used herein, the terms "nano" and "nano-scale" refer to structures that are an average of about 100 nanometers or less in at least one dimension (such as diameter).

A "sample" can be any composition of matter of interest, in any physical state (e.g., solid, liquid, semi-solid, vapor) and of any complexity, such as a biological sample (e.g., a bodily fluid) or environmental sample (e.g., water, soil, slurry, blood, semen, saliva, food, or plant or seed material). Preferably, the sample is a fluid, such as a bodily fluid. The sample may be contained within a test tube, culture vessel, fermentation tank, multi-well plate, or any other container or supporting substrate. The sample can be, for example, a cell culture, human or animal tissue (such as flesh, blood, saliva, semen, vaginal secretion, urine, tears, perspiration, extracellular fluid, etc.), or an environmental sample, such as water, soil, or sludge. The sample can be a small-scale or large scale fermentation.

The "complexity" of a sample refers to the number of different molecular species that are present in the sample.

The terms "body fluid" and "bodily fluid", as used herein, refer to a mixture of molecules obtained from a patient. Bodily fluids include, but are not limited to, exhaled breath, whole blood, blood plasma, urine, semen, saliva, lymph fluid, meningal fluid, amniotic fluid, glandular fluid, sputum, feces, sweat, mucous, and cerebrospinal fluid. Bodily fluid also includes experimentally separated fractions of all of the preceding solutions or mixtures containing homogenized solid material, such as feces, tissues, and biopsy samples.

The term "ex vivo," as used herein, refers to an environment outside of a patient. Accordingly, a sample of bodily fluid collected from a patient is an ex vivo sample of bodily fluid as contemplated by the subject invention. In-dwelling embodiments of the sensor of the invention obtain samples in vivo.

A "patient", as used herein, refers to an organism, including mammals, from which bodily fluid samples are collected in accordance with the present invention. Mammalian species that benefit from the disclosed systems and methods of detection include, and are not limited to, humans, apes, chimpanzees, orangutans, monkeys; and domesticated animals (e.g., pets) such as dogs, cats, mice, rats, guinea pigs, and hamsters.

The terms "molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a continuously varying parameter.

A "solid support" (also referred to herein as a "solid substrate") has a fixed organizational support matrix that preferably functions as an organization matrix, such as a microtiter tray. Solid support materials include, but are not limited to, glass, polacryloylmorpholide, silica, controlled pore glass (CPG), polystyrene, polystyrene/latex, polyethylene, polyamide, carboxyl modified teflon, nylon and nitrocellulose and metals and alloys such as gold, platinum and palladium. The solid support can be biological, non-biological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art. The surface of the solid substrate may contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface can be composed of any of a wide variety of materials, for example, polymers, plastics, resins, polysaccharides, silica or silica-based materials, carbon, metals, inorganic glasses, membranes, or any of the above-listed substrate materials.

"Arraying" refers to the act of organizing or arranging members of a group or library (e.g., an array of different samples or an array of sensing devices that target the same target molecules or different target molecules), or other collection, into a logical or physical array. Thus, an "array" refers to a physical or logical arrangement, e.g., arrangement based on the target molecule of the sensing device. A physical array can be any "spatial format" or "physically gridded format" in which physical manifestations of corresponding group members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or -1536 well, plates (or trays). Sensing devices of the invention can be arranged as arrays or multiplexed for high-throughput assays. For example, multiple sensing devices of the invention can be arranged to detect a single target molecule in many samples, to detect many target molecules in a single sample, or to detect many target molecules in many samples. In some embodiments, multiple electrode systems are arrayed on a single support or multiple supports.

The terms "comprising", "consisting of" and "consisting essentially of" are defined according to their standard meaning. The terms may be substituted for one another throughout the instant application in order to attach the specific meaning associated with each term.

As used in this specification, the singular forms "a", "an", and "the" include plural reference unless the context clearly dictates otherwise. Thus, for example, a reference to "an analyte" includes more than one such analyte. A reference to "an antibody" includes more than one such antibody, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Flames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

MATERIALS AND METHODS

Chemicals. Cortisone (>98%), Hydrocortisone (γ-irradiated, cell culture tested), Anti-cortisol antibody (produced in rabbit), 3α-Hydroxysteroid Dehydrogenase (from *Pseudomonas tsetos*) were purchased from Sigma (St. Louis, Mo.). EDC (1-ethyl-3-[3-dimethylaminopropyl]carbodiimide hydrochloride), EZ-link Sulfo-NHS-LC-Biotin and Strepatavidin conjugated were obtained from Pierce Biotechnology (Rockford, Ill.). DL-Thioctic acid (100%) was purchased from MP Biomedicals (Irvine, Calif.). All measurements were carried out in 0.1 M Phosphate buffered saline (pH 7.2) at room temperature.

Apparatus. Square wave voltammetry measurements were performed using an Autolab PGSTAT30 from Eco chemic N.V. Modified Au nanowires served as working electrode, double junction Ag/AgCl and Pt deposited on the silicon chip served as the reference and counter electrodes, respectively. The electrodes were connected through POGO pins, to external electrochemical analyzer. All electrochemical measurements were performed in a standard three-electrode format. All measurements were performed at room temperature. Fourier transform infrared spectroscopy (FTIR) analysis is performed using Nicolet Avatar 320 FTIR. Hitachi S800 Scanning electron microscope was used to obtain the Scanning Electron Microscopy (SEM) images. Atomic force microscopy was done on a Digital Instruments AFM with Nanoscope III software.

Fabrication of the Electrochemical Biosensor

Figure 2:
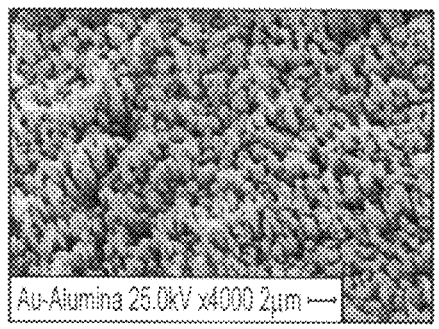
FIG. 2 shows a scanning electron micrograph (SEM) of the 175±25 nm Au nanowires released from alumina template of Au nanowires before the coupling of biotin (top view).
Figure 3:
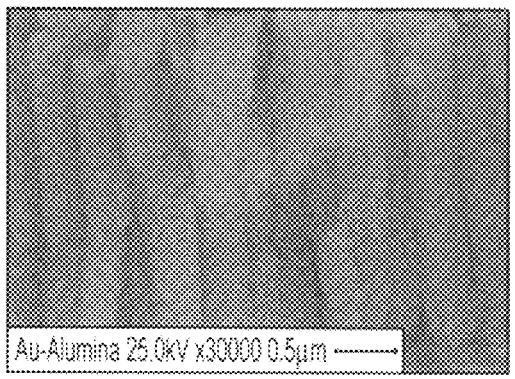
FIG. 3 shows an SEM of electrochemically aligned Au (Gold) nanowires (cross-sectional view).

Preparation of Au nanowires/working electrode. The Au Nanowires and the Micro-fluidic platform were fabricated at the MEMS laboratory of University of South Florida. The Au nanowires were fabricated by electrodeposition of Au into the 200 nm pores of commercial alumina template (Whatmann Inc). A 1-μm aluminum layer was evaporated on one side of the alumina template to act as cathode and platinum mesh acted as anode for electroplating. The electroplating was performed at a current density of 2.5-4 mA/cm$^2$ and 55° C. using Technic 25E plating solution. After electroplating for about 1 hour, the sample was thoroughly rinsed in DI water. Then, the template was dissolved in warm 45% KOH with periodic agitation. This resulted in release of Au nanowires in solution. FIGS. 2 and 3 show the SEM cross-sectional and top view of the Au nanowires of length 175±25 nm and length up to 20 μm released from alumina template. Then, the Au nanowires were collected from KOH by centrifugation at 7000-9000 RPM. The supernatant was decanted and replaced with clean methanol. The nanowires were sonicated for 1 minute and this protocol of collection/solvent addition/sonication was repeated three times to completely clean the nanowires.

Fabrication of micro-fluidic chip. The micro-fluidic chip was then fabricated in (100) silicon substrate (2.5×2.5 mm). FIG. 4 shows the micro-fluidic chip/test cell with electrodes and electrical connections. First, the "assembly" lines and counter electrode were fabricated in Platinum (Pt) (FIGS. 4B and 4C). This was done by photolithography, subsequent e-beam evaporation and lift-off of Ti/Pt electrodes. Ti acts as adhesion layer for Pt. This was followed by fabrication of 60 μm tall micro-fluidic chamber in SU-8 (Microchem, Newton, Mass.) to hold the reagents (FIG. 4D). The SU-8 chamber was hard baked at 180° C. for 3 minutes to prevent any out-gassing or contamination.

Integration of Au nanowires into the Micro-fluidic chip. The next step was to align the released Au nanowires in methanol on to the "assembly lines" of the micro-fluidic chip (FIG. 4). This is to create the "aligned" working electrode of Au nanowires for electrochemical measurement. The directed assembly of nanowires bridging the "assembly" lines was achieved utilizing dielectrophoresis technique, which involves selective assembly of neutral particles in a liquid dielectric medium by non-uniform electric fields (Boote et al., 2005). Dilute suspensions (200 μL, 10$^7$ wires/mL) of the nanowires were dispensed on to the "assembly" lines and alternating voltage ranging from 10 to 50 Vrms was applied for about 15-45 seconds between the lines. This resulted in movement of nanowires towards regions of highest field intensity, and subsequent alignment of the nanowires bridging the "assembly" lines. The assembly was monitored by studying the series current and later verified by a scanning electron microscope (SEM). The integrated Au nanowire/micro-fluidic chip was later cleaned to remove any excess nanowires and left overnight for drying.

Figure 5:
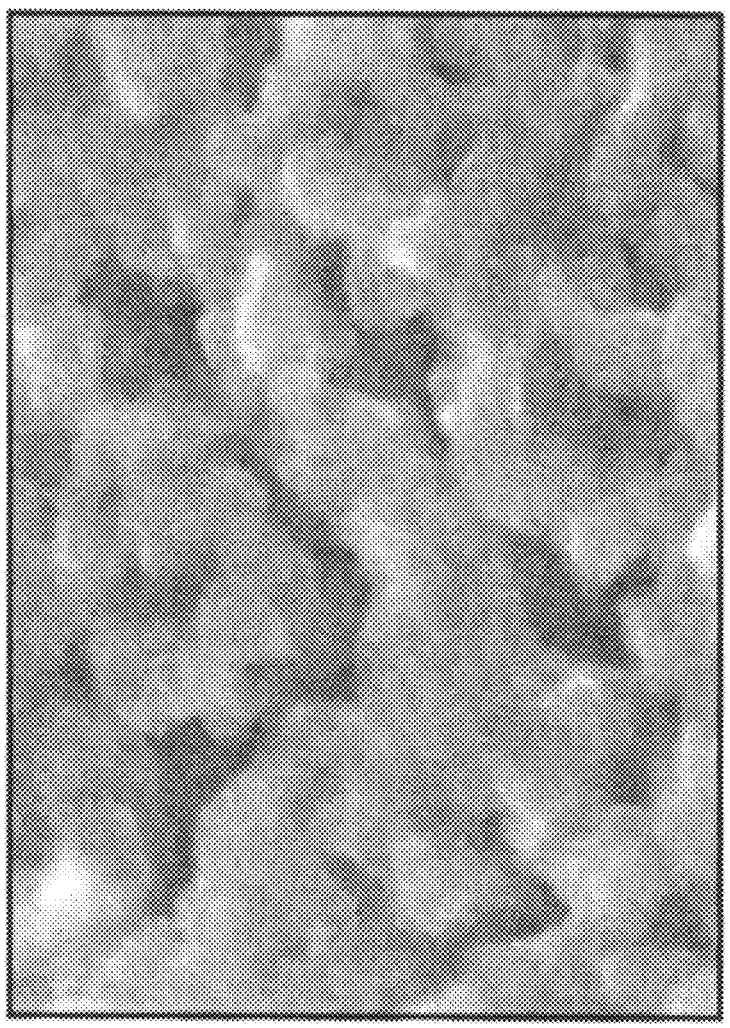
FIG. 5 shows an SEM of Au nanowires after coupling with biotin/avidin (top view).

Surface functionalization of Au Nanowires with cortisol antibodies and dehydrogenase. First, the Au nanowires were cleaned in piranha solution (1:3 Hydrogen peroxide and sulphuric acid) and then, rinsed in excess deionized (DI) water (18.2 MΩ, Millipore Milli Q system). Next, the Au nanowires were activated with 2% (w/w) thioctic acid in absolute ethanol with shaking. The nanowires were then rinsed in ethanol twice and dried. Next, the Au nanowires were immobilized using carboxyl-terminated coupling with 0.2 M EDC and 0.05 M NHS-LS biotin (Pierce Chemical) in DI water. Finally, 250 μg/mL, of streptavidin (Pierce chemical) in PBS was specifically immobilized over Au surface and incubated at 4° C. overnight. FIG. 5 shows the SEM image of Au nanowires functionalized with streptavidin. The biotin/avidin linkage is one of the strongest known biological interactions (Diamandis et al., 1991) and can be used for further linking of Au nanowires to cortisol antibodies, which is further confirmed with FTIR spectroscopic method carbonyl stretching frequency amide I (1695 cm-1) and amide II C—N (1646 cm-1) stretches from the resonating peptide backbone intensity is considerably reduced peak at 1720 cm. Carbonyl stretches at 1640 cm-1 and broad O—H stretching between 3500 and 3000 cm-1 were observed. The untreated reagents present over the Au nanowires were washed in PBS solution.

Electrochemical Measurements. Square wave voltammogram were recorded at room temperature in a custom-built test cell (FIG. 4A). All the tests were performed in the PBS buffer pH 7.2 and blood serum was used to study the interference in the measurement signal. Baseline/zero line signals were obtained using blank 0.1 M PBS. The calibration curves were obtained using increased concentration of mixture of cortison and converting it into cortisol using 3α-Hydroxysteroid Dehydrogenase. Cortisone (>98%) was dissolved in PBS and with a few drops of Triton X-100. Prior to use, the test cell was thoroughly cleaned using DI water and subsequently with PBS solution. Square wave voltammograms of detected cortisol were recorded by applying the negative going potential scan with frequency of 8 Hz, amplitude 20 mV and potential step of 4 mV. At the same time, 3α-Hydroxysteroid dehydrogenase was introduced into the system and detected electrochemically using functionalized Au nanowires. The response curves for all concentrations were recorded under identical conditions.

Assay procedure. Each time 25 μL of solution was introduced into the cell which contain different concentration of cortison allow 5 seconds to react with 3α-hydroxysteroid dehydrogenase which introduced into the system separately. After that the functionalized electrode (Au nanowires coupled with antibodies for cortisol) was scanned in the range of 0.02 V-0.08 V. The concentration of the 3α-hydroxysteroid dehydrogenase in the system was detected with another set of Au nanoelectrodes to understand the increase in the signal after the injection of fixed amount of 3α-hydroxysteroid dehydrogenase.

The reaction involved is:

11-keto metabolite cortisone(cortisone).+11-Hydroxysteroid dehydrogenase (type 1(11HSD1)→Glucocorticoids(Cortisol)

EXAMPLE 1

SEM Investigations of Functionalized Gold Nanowires

The 11β-hydroxysteroid dehydrogenase type 2 enzyme (11βHSD2) metabolizes glucocorticoids into their inactive 11-keto metabolites (Cortison). Although the type 1 enzyme (11βHSD1) displays both oxidative and reductive activity, to date 11βHSD2 has been shown to have dehydrogenase activity only. Although bidirectional, in vivo it is believed to function as a reductase generating active glucocorticoid at a pre-receptor level, enhancing glucocorticoid receptor activation. However, the detection of inactive and active forms of cortisol is important to understand the role of cortisol in particular pathological and psychological disorders. In the proposed scheme, the present inventors measured cortisol present in the system in the form of cortisol as well as its conversion form from the cortison which is present in inactive form. These findings will be highly important to understand the profiles for a wide range of steroids often used in clinical practice and many disorders where it is important to know the overall concentration of the cortisol present in the system. This detection is based on competitive binding of cortisol, in free state as well as in the form of cortisone, to a high-affinity, high-specificity, anticortisol monoclonal antibody immobilized over Au (gold nanowires) and it has a broad dynamic detection range of 10 μM-80 μM. Further, another set of nanowires was functionalized with hydroxysteroid dehydrogenase, which is used to reduce cortisone to cortisol to enhance the signal by capturing it with cortisol antibodies immobilized over another set of electrode wires. In each measurement of cortisone, a fixed amount of 3α-Hydroxysteroid dehydrogenase was introduced into the system and its concentration was detected separately with another set of functionalized Au nanowires. The curve of the measurements of 3α-Hydroxysteroid dehydrogenase was found to be linear. It suggests that the cortisone conversion into cortisol is dependent upon the amount of the 3α-Hydroxysteroid dehydrogenase present in the system and it is directly proportional to the concentration of cortison present in the system. Enzyme fragment complementation (EFC) technology provides a sensitive and homogeneous method for measuring analytes by enzymatically amplifying the signal. These fragments are inactive separately but, in solution, they rapidly recombine to form an active enzyme by the process of complementation (scheme shown in FIG. 1).

Scanning electron micrograph (SEM) of the gold nanowires show a smooth and homogeneous surface before the immobilization of the cortisol antibodies as shown in FIGS. 2 and 3. Further, in the SEM image of the covalently linked cortisol antibodies to the gold nanowires are clearly visible (data not shown). With a similar technique, the coupling of the hydroxysteroid dehydrogenase with Au nanowires was confirmed (data is also not shown).

EXAMPLE 2

AFM Analysis of the Functionalized Au (Gold) Nanowires

Figure 6:
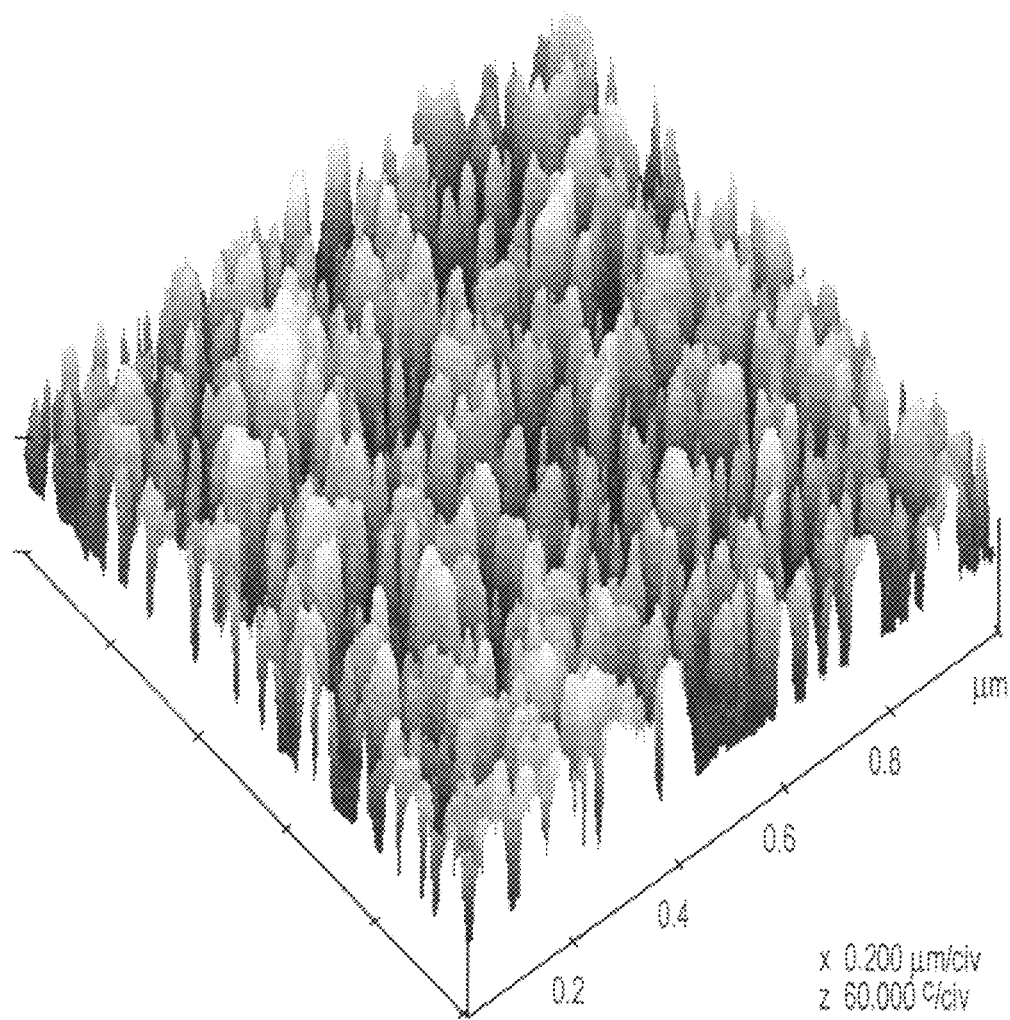
FIG. 6 shows an atomic force micrograph (AFM) of gold nanowires before coupling to cortisol.
Figure 7:
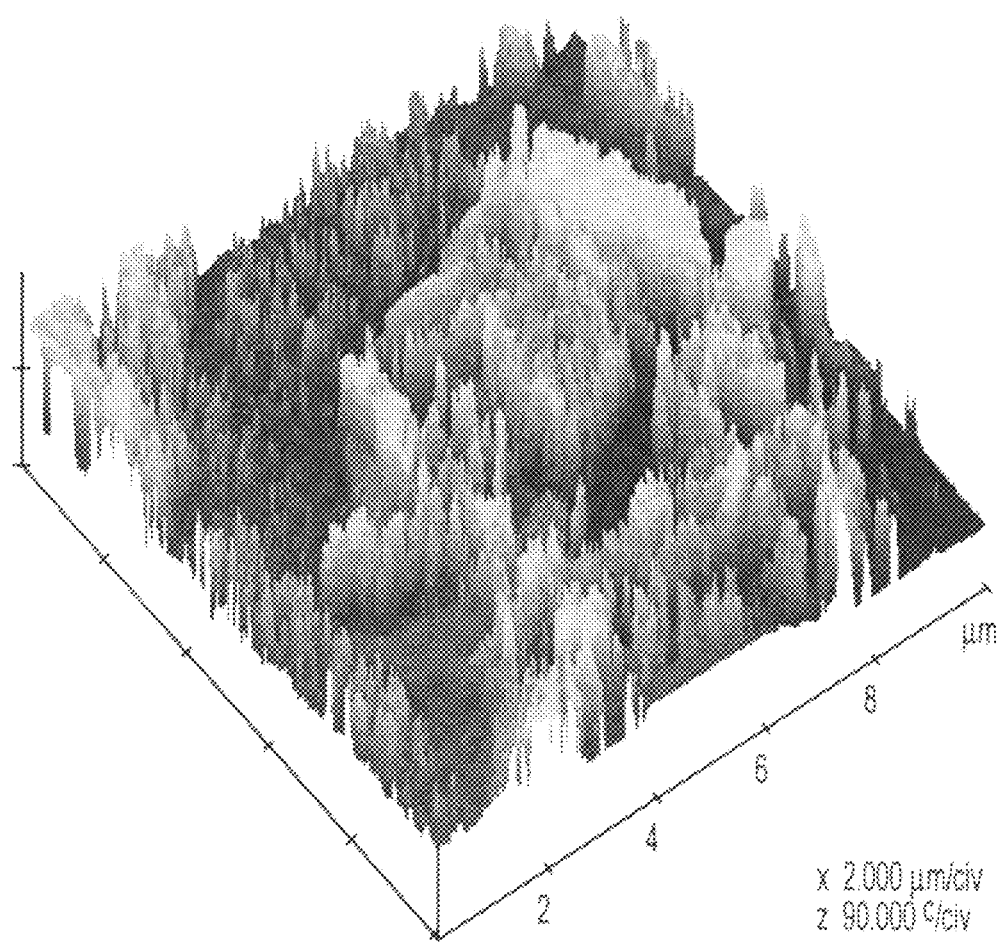
FIG. 7 shows an AFM of gold nanowires after coupling to cortisol.

The coupling of the cortisol antibodies with the Au nanowires was further confirmed with atomic force microscopy (AFM). FIGS. 5 and 6 show the AFM image of the nanowires before and after immobilization of cortisol antibodies. The coupling can be seen clearly as increase in the roughness of the surface in the AFM image (FIG. 6). The figure shows smooth surface of the Au nanowires before coupling and after the coupling of cortisol antibodies the roughness of the Au nanowires surface has changed.

EXAMPLE 3

Electrochemical Response Studies of the Cortisol Detection

Figure 8A:
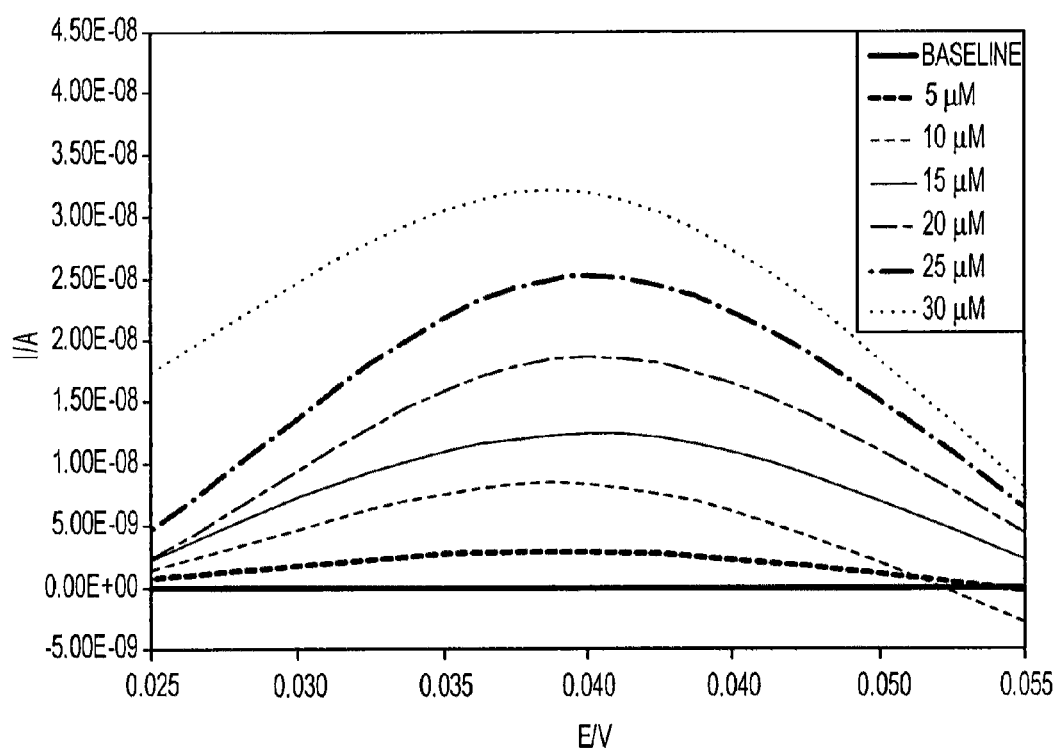
FIGS. 8A and 8B show an SW voltammogram of potential (0.025 to 0.055 V) versus current at different concentration of hydroxylase (FIG. 8A), and a calibration curve (FIG. 8B).
Figure 8B:
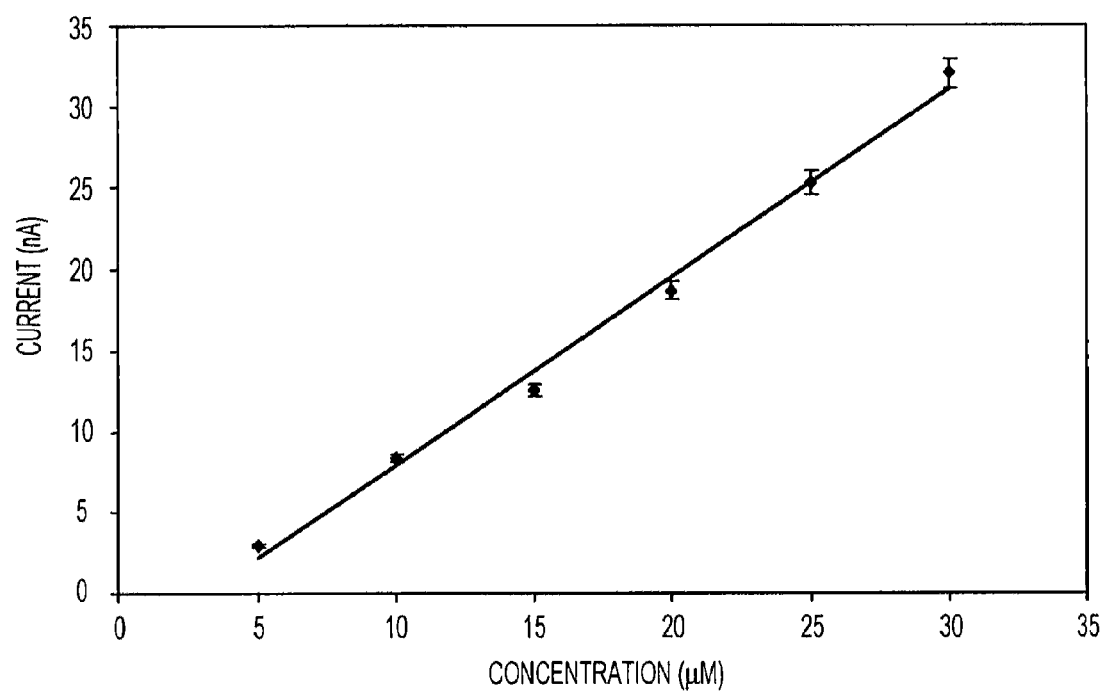

The biomolecules can be sensitively detected by using the square wave voltammogram technique. The scheme for this particular biosensor involved converting cortisone into cortisol using 3α-hydroxysteroid dehydrogenase, and capturing the cortisol over the electrode comprising Au nanowires with coupled cortisol antibodies, and electrochemically detecting the target (cortisol) using negative going potential. After scanning several times in different ranges, the detection range was found between 0.0-0.055 V, which is appropriate enough to avoid interfering signals. An increase in anodic peaks with respect to cortison as well 3α-Hydroxysteroid dehydrogenase concentrations using the same set of electrode configuration in the system confirms the conversion of cortison into cortisol. The concentration of the 3α-Hydroxysteroid dehydrogenase was measured spartanly with another set of functionalized Au nanowire electrodes. It was found the graph is linear (FIGS. 8A and 8B), which may be because the total concentration of cortisol depends upon the amount of enzyme available for the reaction into the system. The scan was repeated after bringing the initial current to normal stage and again scanned after introducing higher concentration of cortison solution into the cell. For the baseline correction, PBS was used to avoid any kind of interference in the solution. The possibility of increase in the current is due to the oxidation of antibodies-cortisol complex over the gold nanowires as the conductivity the Au nanowires are higher due to the increase in the surface area of the electrode and aligned nature.

EXAMPLE 4

Calibration Plot for Determination of Cortisol

The calibration line was created by taking the peak anodic voltage values for each curve and plotting this voltage value for each cortisol level that linear response fit observed for hydrocortisol within the concentration range.

$$\text{Current(nA)}=1.16 \cdot [\text{hydrocortisol}(\mu M)]-3.61 \quad (1)$$

Figure 9A:
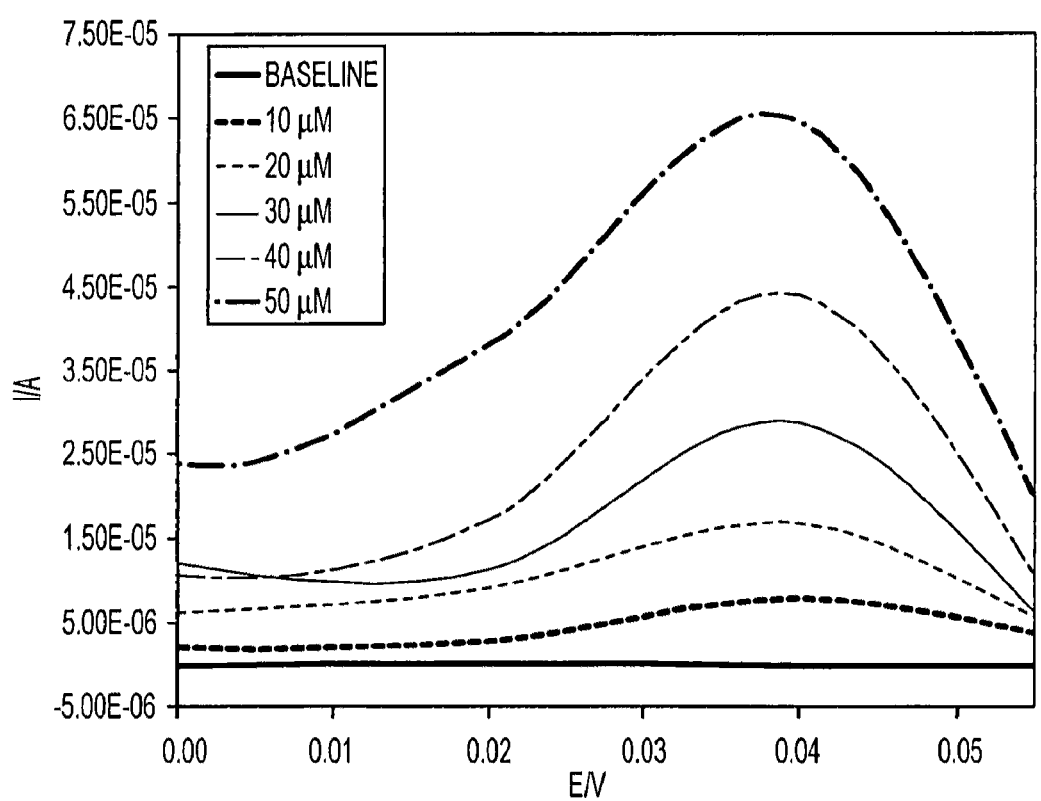
FIGS. 9A and 9B show SW voltammograms of potential (0.0 to 0.055 V) versus current (A) at different concentration of cortisol.
Figure 9B:
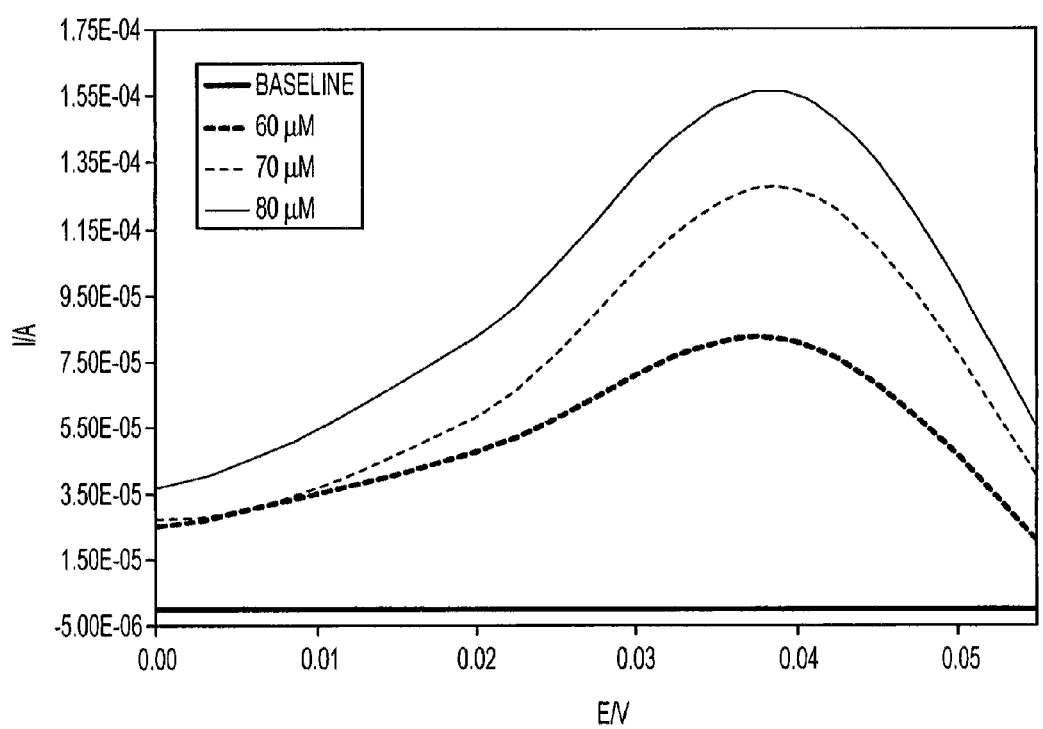
Figure 10:
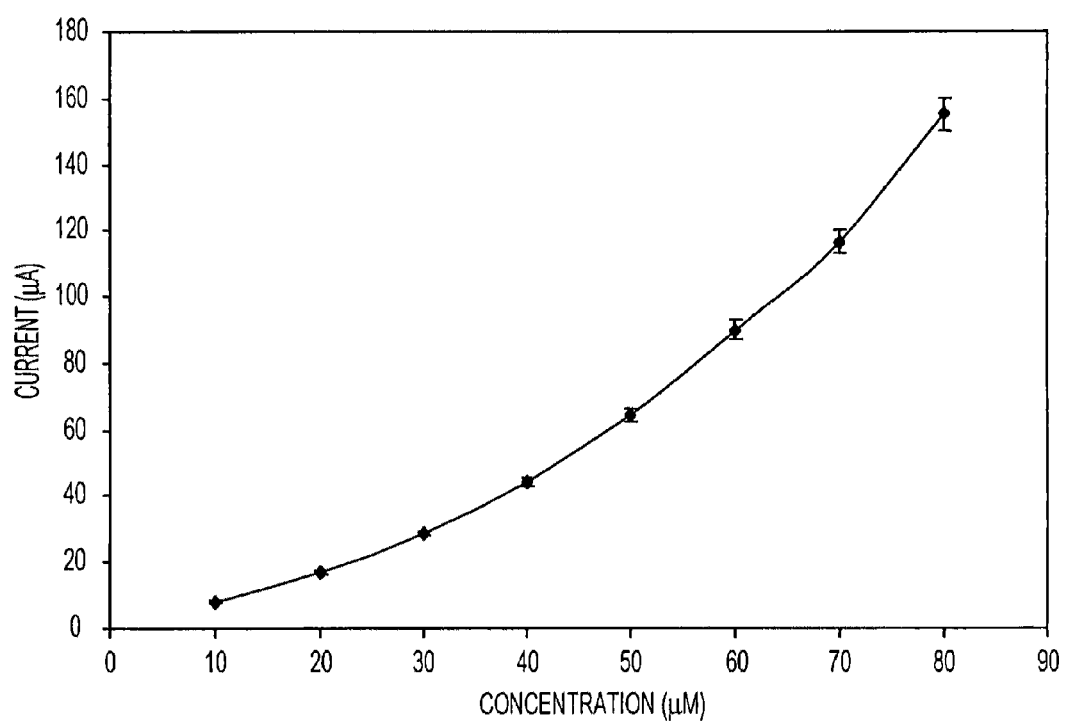
FIG. 10 shows a calibration curve of the cortisol detection.

For cortisol, the calibration curve and electrochemical response are shown in FIGS. 9 and 10. It follows a polynomial equation:

$$\text{Current}(\mu A)=0.0223[\text{cortisol}(\mu M)]^2+0.0514[\text{cortisol}(\mu M)]+6.1735 \quad (2)$$

The sensitivity for hydrocortisol can be calculated to 0.80 nA/μM, while that for cortisol is found to be 0.89 μA/μM. This improved sensor response and sensitivity is due to enhanced electrical conductivity and electron transfer capability found in Au nanowires.

The stability of the biosensor was confirmed with 20 runs of 20 μM analysis of the cortison with same functionalized electrode. The error was in the range of 1-1.5% of the detection curve (data is not shown).

EXAMPLE 5

Interferences

Interferences were studied with blood serum mixed to the solution. Interfering species in blood to cortisol detection such as cholesterol, ascorbic acid and uric acid at normal levels have no effect on the electrochemical response, because of the efficient electrode modification scheme, low working potentials and relatively small concentration of the metabolites.

EXAMPLE 6

Ultrasensitive Detection of Prostate Cancer Biomarker (Prostate-Specific Antigen)

A. Detection of Prostate Cancer Antigen, PSA, by MAP Technology.

Prostate-specific antigen (PSA) is a protein produced by the cells of the prostate gland. The PSA levels in blood indicate whether further tests are necessary for prostate cancer. The following ranges are used in clinical diagnosis of prostate cancer with some variation: 0 to 2.5 ng/ml is low 2.6 to 10 ng/ml is slightly to moderately elevated 10 to 19.9 ng/ml is moderately elevated 20 ng/ml or more is significantly elevated. Because various factors can cause PSA levels to fluctuate, one abnormal PSA test does not necessarily indicate a need for other diagnostic tests. Toward developing a multiplexed test for prostate cancer, the present inventors have tested MAP technology for detection of PSA antigen.

B. Micro Fluidic Device for the Detection of Prostate Antigen.

To produce the test device, the Au nanowires and the microfluidic platform were fabricated at the MEMS laboratory of University of South Florida. The Au nanowires were fabricated by electro deposition of Au into the 200 nm pores of commercial alumina template (Whatmann Inc). A 1-μm aluminium layer was evaporated on one side of the alumina template to act as cathode and platinum mesh acted as anode for electroplating. The electroplating was performed at a current density of 2.5-4 mA/cm2 and 55° C. using Technique 25E plating solution. Then, the micro-fluidic chip was then fabricated in (100) silicon substrate (2.5×2.5 mm). First, the "assembly" lines and counter electrode were fabricated in Platinum (Pt). This was then by photolithography, subsequent ebeam evaporation and lift-off of Ti/Pt electrodes. Ti acts as adhesion layer for Pt. This was followed by fabrication of 60 μm tall micro-fluidic chamber in SU-8 (Microchem, Newton, Mass.) to hold the reagents. The SU-8 chamber was hard baked at 180° C. for 3 minutes to prevent any out-gassing or contamination. The next step was to align the released Au (gold) nanowires in methanol on to the "assembly lines" of the micro-fluidic chip. This created the "aligned" working electrode of Au nanowires for sensitive electrochemical measurement. The directed assembly of nanowires bridging the "assembly" lines was achieved utilizing dielectrophoresis technique, which involves selective assembly of neutral particles in aliquid dielectric medium by non-uniform electric fields (Boote et al., 2005). Dilute suspensions (200 μL, 107 wires/mL) of the nanowires were dispensed on to the "assembly" lines and alternating voltage ranging from 10 to 50 Vrms (root mean squared voltage.) was applied for about 15-45 seconds between the lines. This resulted in movement of nanowires towards regions of highest field intensity, and subsequent alignment of the nanowires bridging the "assembly" lines.

C. Surface Functionalization and Characterization of Au (Gold) Nanowires with PSA Antibodies.

In the first step, the Au nanowires were cleaned with piranha solution (1:3) hydrogen peroxide and sulphuric acid) and then, rinsed using excess of deionized (DI) water (18.2 MΩ, Millipore Milli Q system). In the second, step the Au nanowires were activated by shaking with 2% (w/w) thioctic acid in absolute ethanol. The nanowires were then rinsed with ethanol twice and dried. PSA antibody was directly immobilized using the streptavidin/biotin linkage.

D. Electrochemical Measurements.

Figure 11:
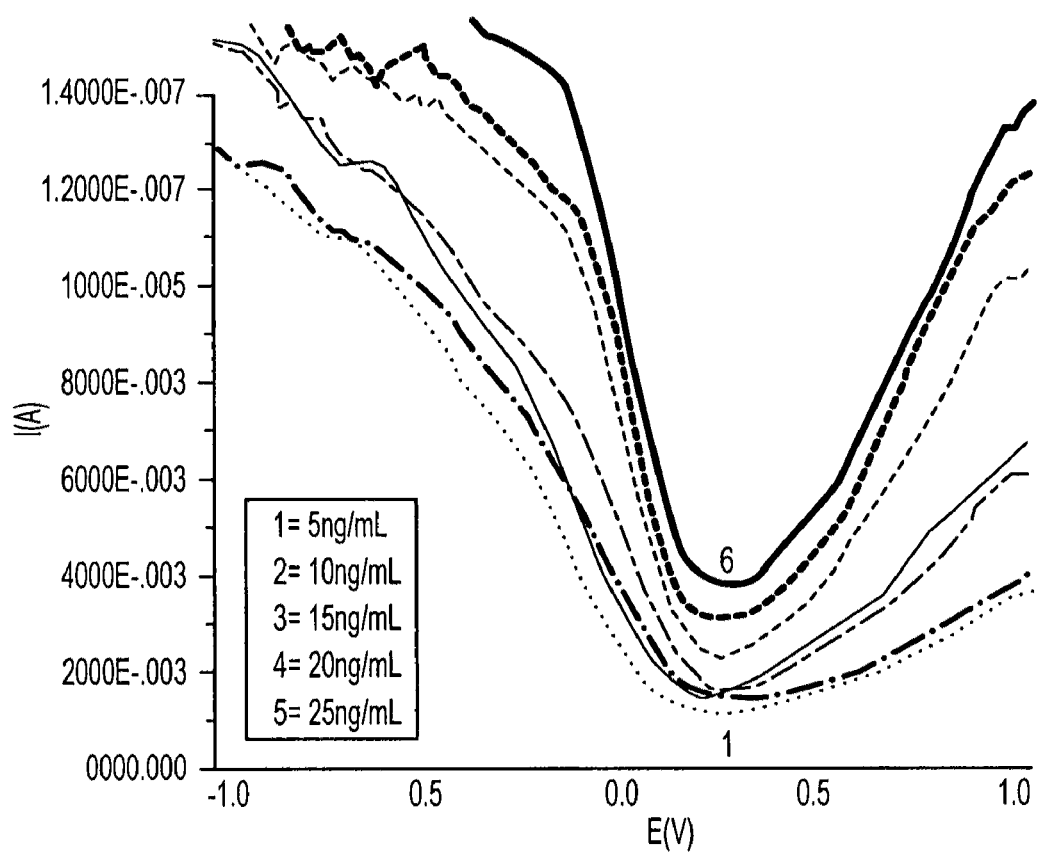
FIG. 11 shows a cyclic voltammogram for the detection of prostate specific antigen (PSA) from 5 ng/mL to 30 ng/mL, with each measurement recorded in 5 seconds. Analysis was carried out in PBS buffer (7.2 pH) using functionalized gold nanowires in a micofluidic device of the invention.
Figure 12:
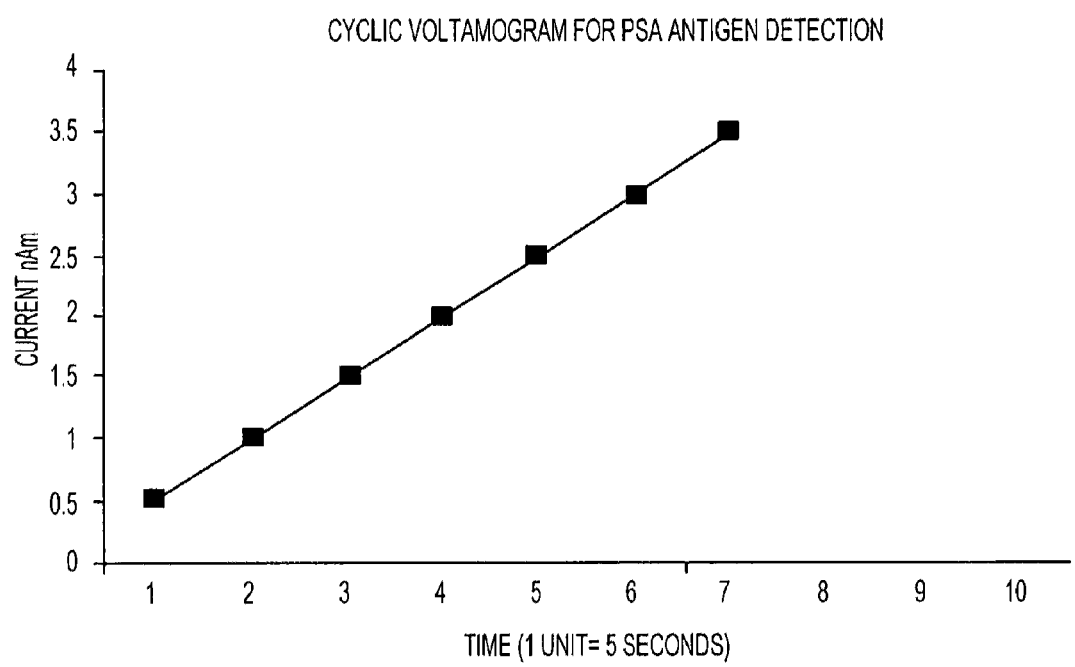
FIG. 12 shows a calibration curve for the PSA detection.
Figure 13B:
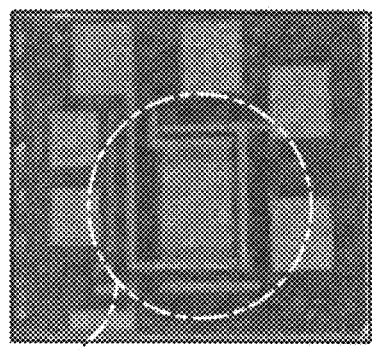
FIGS. 13A-13E show A) a microfluidic device with a top lid connected with a tube to introduce the sample; B) gold nanowires on the chip; C) a SEM of gold nanowires; D) a micro fluidic device with a lid for sample testing; and E) an enlarged view of a microchip with gold nanowires.
Figure 13A:
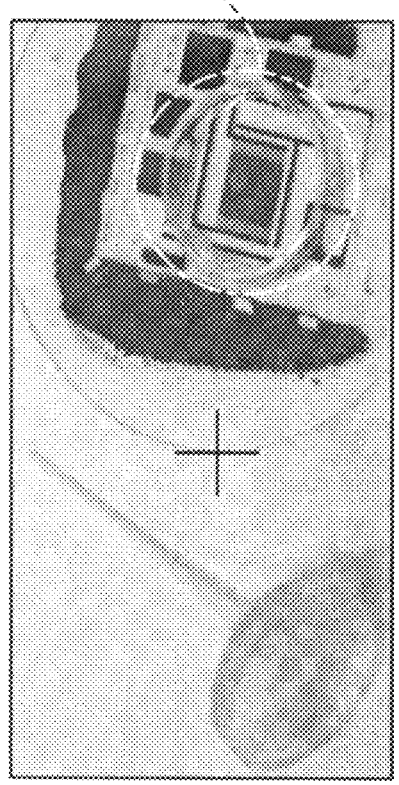
Figure 13E:
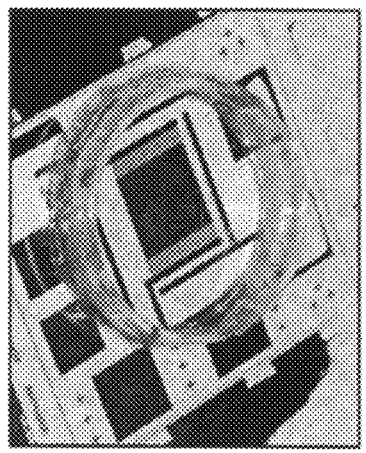
Figure 13D:
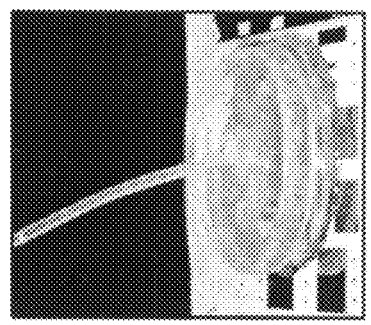
Figure 13C:
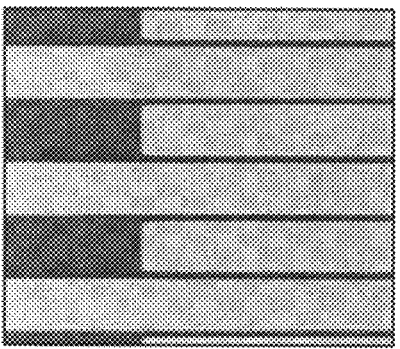

Cyclic wave voltammogram were recorded at room temperature in a custom-built test cell. All the tests were performed using the PBS buffer pH 7.2. Baseline line signals were obtained using blank 0.1 M PBS. The calibration curves were obtained using increased concentration of PSA antigen. Each time 10 μL of solution was introduced trough tube into the cell, which contains different concentration of PSA antigen. The results of voltagram analysis are shown in FIGS. 11 and 12. The results demonstrate that PSA levels can be measured at the using level of 2.5 to 10 ng/ml, which is in the range of clinical sensitivity.

EXAMPLE 7

Detection of 8-Isoprostene, a Biomarker of Oxidative Stress in Chronic Lung Diseases and Lung Cancer Toward developing a MAP device for detection system for lung cancers, a MAP-based detection of 8-isoprostane, a prostaglandin isomer formed by free radical catalysed peroxidation of arachidonic acid was established. Similar to nitrotyrosine, 8-isoprostane is considered a valid marker of antioxidant deficiency and oxidative stress, and its use has been hampered by difficulty in measuring its concentration. 8-isoprostanes exert biological activity including, increased smooth muscle and vascular permeability and constriction, increased airway hyperresponsiveness and obstruction, plasma exudation and epithelial cell activation, disruption and death. 8-isoprostane is the "gold standard" of clinical markers of oxidant stress and the class of prostanoids and the $F_2$-isoprostanes have become potential pharmacological targets it is one of the most abundant isomers formed in vivo is produced in many animal species and exhibits biological activity. The concentration of 8-isoprostane is elevated in heavy smokers. A cascade of complex inflammatory events is associated with both the malignant and nonmalignant sequelae of the lung epithelial cells and 8-isoprostane can be a marker measurable in urine and sputum or sputum cells.

Figure 14:
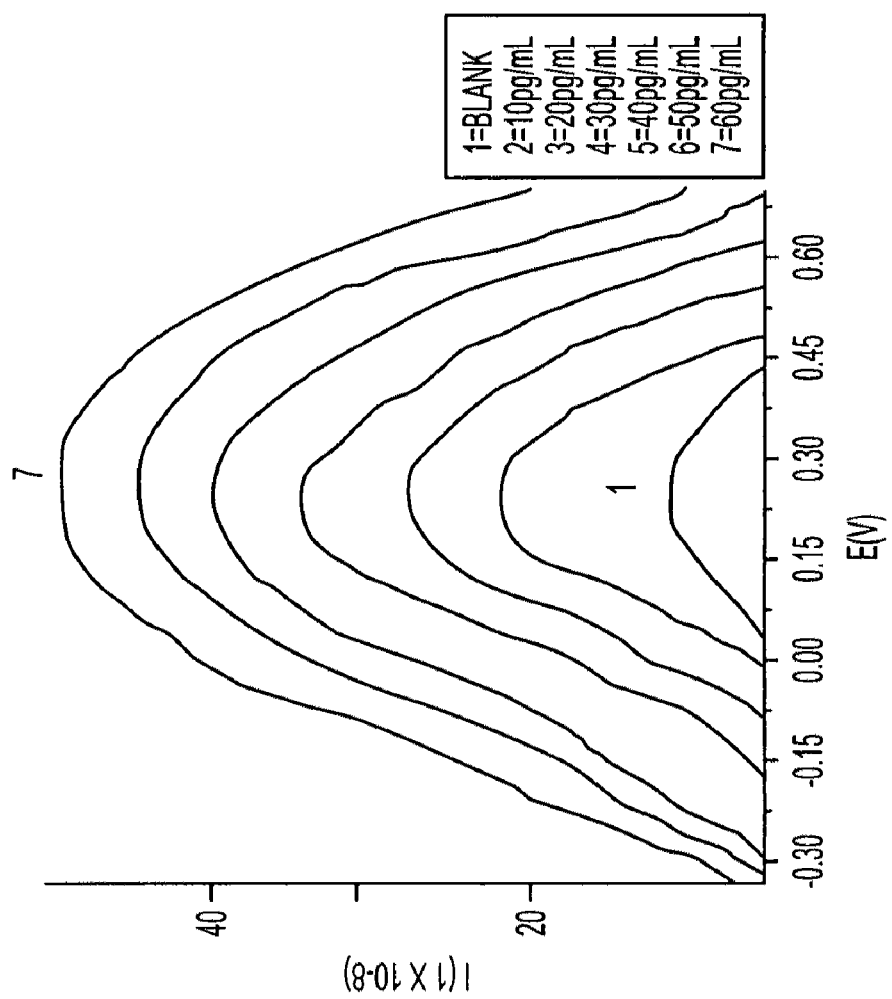
FIG. 14 shows the results of a square-wave voltametry technique for the estimation of 8-isoprostane.
Figure 15:
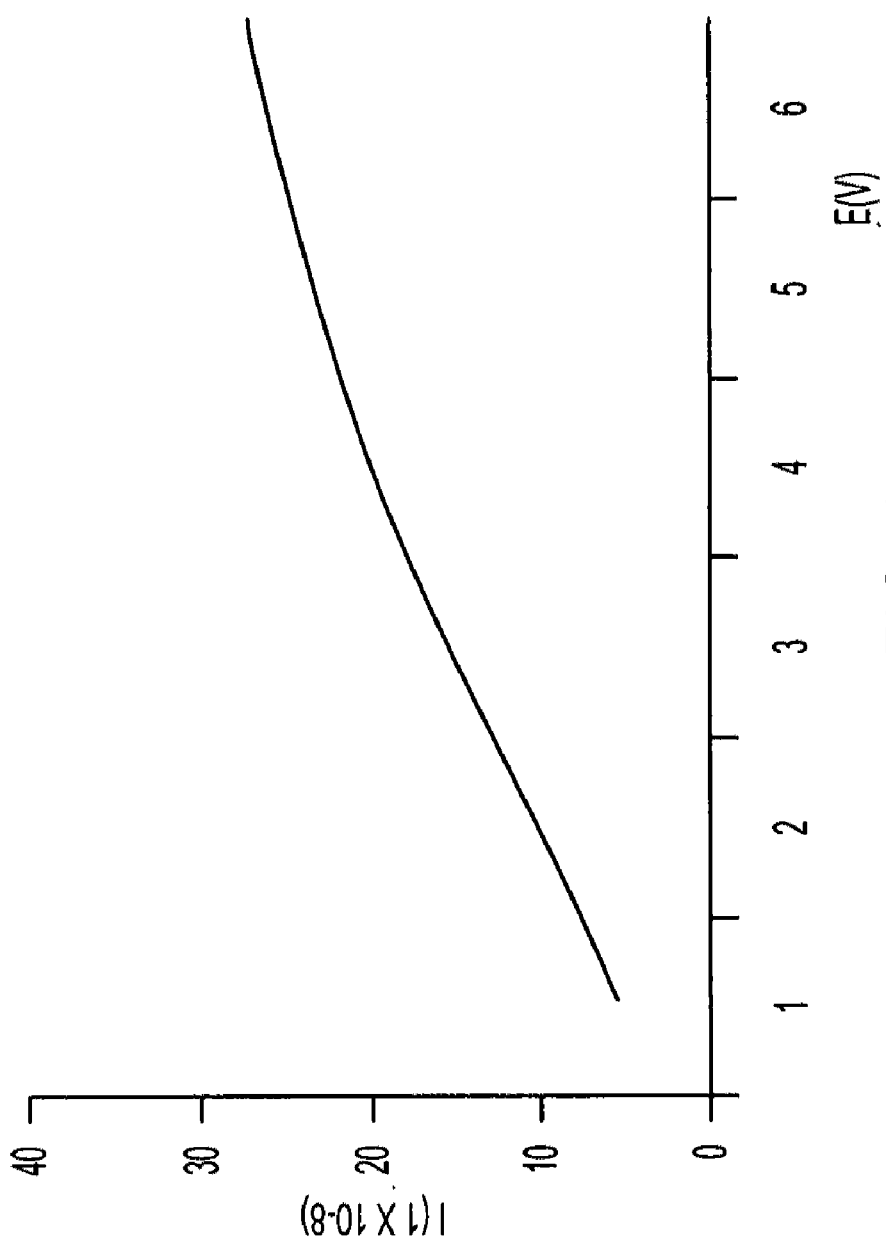
FIG. 15 shows a standard curve for the estimation of 8-isoprostane.

For the detection of 8-isoprostane, the microchip was fabricated over silicon wafer, as described for cortisol with some modification. FIGS. 13A-13E shows the photographs of assembled microfluidic device with top lid connected with tube to introduce the sample, gold nanowires on the chip, SEM of gold nanowires, microfluidic device with lid for sample testing, and an enlarged view of microchip with gold nanowires (FIGS. 13A-13E). To develop detection method for 8-isoprostane the antibodies of 8-isoprostane were immobilized over the gold nanowires using thiol-chemistry and further modified gold nanowires are used to detect the 8-isoprostane. The result shows this technique can detect 8-isoprostene at nano-mol level (0-60 nmol) by using an electrochemical technique (square wave voltammetery). The detection time is 5 seconds. This approach can be used for detection of 8-isoprostene in a patient's breath, for example, by blowing breath over the microchip, and analysis can be completed in 5 minutes (see FIGS. 14 and 15).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Abdallah, B. M. et al. *European Journal of Clinical Investigation*, 2005, 35:627-634.
2. Appel, D. et al. *Anal Bioanal Chem.*, 2005 September, 383(2):182-6; Epub 2005 Oct. 12.
3. Boote, J. J. and Evans, S. D. *Nanotechnology*, 2005, 16:1500-1505.
4. Diamandis, E. P. and Christopoulos, T. K. *Clin. Chem.*, 1991, 37:625-636.
5. Galimberti, C. A. et al. *Epilepsia*, 2005, 46(4):517-523.
6. Gatti, R. et al. *J Chromatogr B Analyt Technol Biomed Life Sci.*, 2005 Sep. 25, 824(1-2):51-6.
7. Jezova, D. *Endocrine*, 2005 December, 28(3):287-94. Review
8. Kurina, L. M. et al. *Stress and Health*, 2004, 20:53-63.
9. Liu, H. et al. *Clinical Endocrinology*, 2005, 63:642-649.
10. Quinkler, M. and Stewart, P. M. *Journal of Clinical Endocrinology & Metabolism*, 2003, 88(6):2384-2392.
11. Nomura, S. et al. *Clin. Chim. Acta*, 1996 Dec. 9, 256(1):1-11.
12. Oosterlaan, J. et al. *Psychiatry Res.*, 2005 Mar. 30, 134(1):1-10.
13. Petkus, M. M. et al. *Analytical Chemistry*, 2006, 78:1405-1411.
14. Stewart, P. M. et al. *J. Clin Endocrinol Metab.*, 1999 March, 84(3): 1022-7.
15. Wren, J. D. and Garner, H. R. *Journal of Biomedicine and Biotechnology*, 2005, 2:104-112.

We claim:

1. A sensor device comprising an electrode system and a microfluidic platform, wherein the electrode system comprises at least one working electrode comprising an array of aligned, linear nano-wires; and at least one counter electrode, wherein the aligned, linear nano-wires have at least one binding agent coupled thereto, wherein the binding agent exhibits binding affinity for a target molecule, wherein the microfluidic platform comprises at least one solid support having a surface, and having at least one fluid passage and having at least one sample inlet, wherein the array of aligned, linear nano-wires projects from the surface of the at least one solid support wherein the array of nanowires is aligned to bridge a space between two conductive assembly lines that are deposited on the surface of the at least one solid support, and wherein the inlet is in fluid communication with the working electrode.

2. The sensor device of claim 1, further comprising an enzyme coupled to the working electrode, wherein the enzyme acts on a substrate that is an alternative form of the target molecule to thereby produce the target molecule.

3. The sensor device of claim 1, wherein the binding agent is a monoclonal antibody, polyclonal antibody, or fragment thereof.

4. The sensor device of claim 1, wherein the aligned, linear nano-wires comprise gold.

5. The sensor device of claim 1, wherein the counter electrode comprises platinum.

6. The sensor device of claim 1, further comprising at least one reference electrode.

7. The sensor device of claim 6, wherein the reference electrode comprises silver/silver chloride.

8. The sensor device of claim 1, wherein the counter electrode comprises platinum deposited on a silicon chip.

9. The sensor device of claim 1, wherein the working electrode comprises aligned, linear gold nano-wires, the counter electrode comprises platinum deposited on a silicon chip, and the device further comprises at least one reference electrode comprising silver/silver chloride.

10. The sensor device of claim 1, wherein the target molecule is a biological analyte.

11. The sensor device of claim 1, wherein the target molecule is a biomarker of human or animal disease.

12. The sensor device of claim 1, wherein the binding agent further comprises a detectable label indicating when the binding agent has bound the target molecule.

13. The sensor device of claim 1, further comprising an electrochemical analyzer, wherein a signal is sent from the working electrode to the electrochemical analyzer upon binding of the target molecule to the binding agent.

14. The sensor device of claim 1, wherein the target molecule comprises prostate-specific antigen.

15. The sensor device of claim 1, wherein the target molecule comprises 8-isoprostane.

16. The sensor device of claim 1, wherein the at least one passage of the microfluidic platform comprises a network of channels.

17. The sensor device of claim 1, wherein the at least one inlet comprises a plurality of inlets for a plurality of samples.

18. The sensor device of claim 1, wherein the counter electrode functions as both a counter electrode and a reference electrode.

19. The sensor device of claim 1, wherein the counter electrode functions as both a counter electrode and the solid support.

20. The sensor device of claim 1, wherein each of the aligned, linear nano-wires has a first end that is attached to at least one solid support.

21. The sensor device of claim 1, wherein the aligned, linear nano-wires have a positive length-to-width ratio, and wherein the length and a free end of each of the aligned, linear nano-wires is accessible to the sample.

22. The sensor device of claim 1, wherein each of the aligned, linear nano-wires has a positive length-to-width ratio and a first end that is attached to the at least one solid support, and wherein the length and free end of each of the aligned, linear nano-wires is accessible to the at least one sample.

23. The sensor device of claim 1, wherein the binding agent exhibits binding affinity for cortisol.

24. The sensor device of claim 23, further comprising an enzyme coupled to the working electrode, wherein the enzyme acts on a substrate that is an alternative form of the cortisol to thereby produce the cortisol.

25. The sensor device of claim 24, wherein the enzyme is hydroxysteroid dehydrogenase, and wherein the substrate is cortisone.

26. The sensor device of claim 1, wherein the array of aligned, linear nano-wires are aligned by dielectrophoresis.

27. A method for detecting the presence of a target molecule in a sample, comprising:

providing a sensor device comprising an electrode system and a microfluidic platform, wherein the electrode system comprises at least one working electrode comprising an array of aligned, linear nano-wires; and at least one counter electrode, wherein the aligned, linear nano-wires have at least one binding agent coupled thereto, wherein the binding agent exhibits binding affinity for a target molecule, wherein the microfluidic platform comprises at least one solid support having a surface and having at least one fluid passage and having at least one sample inlet, wherein the array of aligned, linear nano-wires projects from the surface of the at least one solid support, wherein the array of nano-wires is aligned to bridge a space between two conductive assembly lines that are deposited on the surface of the at least one solid support, and wherein the inlet is in fluid communication with the working electrode;

inputting the at least one sample in the at least one inlet; and contacting the at least one sample with the at least one working electrode.

28. The method of claim 27, wherein the sample is a bodily fluid.

29. The method of claim 27, wherein the sample is blood.

30. The method of claim 27, wherein the sample is an environmental sample.

31. The method of claim 30, wherein the environmental sample is water.

32. The method of claim 31, wherein the environmental sample is waste water.

* * * * *

UNITED STATES PATENT AND TRADEMARK OFFICE
CERTIFICATE OF CORRECTION

PATENT NO. : 8,349,604 B2  
APPLICATION NO. : 11/747713  
DATED : January 8, 2013  
INVENTOR(S) : Shyam S. Mohapatra and Arun Kumar Page 1 of 1

It is certified that error appears in the above-identified patent and that said Letters Patent is hereby corrected as shown below:

In the Specifications

Column 22,  
Line 56, "(Flames" should read --(Hames--

Column 29,  
Line 59, "support wherein" should read --support, wherein--  
Line 59, "nanowires" should read --nano-wires--

In the Claims

Column 30,  
Line 56, "nano-wires is" should read --nano-wires are--

Signed and Sealed this  
Twenty-third Day of April, 2013

Teresa Stanek Rea  
*Acting Director of the United States Patent and Trademark Office*